US007341552B2

(12) United States Patent
Zhang et al.

(10) Patent No.: US 7,341,552 B2
(45) Date of Patent: Mar. 11, 2008

(54) GENE SETS FOR GLIOMA CLASSIFICATION

(75) Inventors: Wei Zhang, Houston, TX (US); Greg Fuller, Houston, TX (US); Ed Dougherty, College Station, TX (US); Kenneth Hess, Houston, TX (US)

(73) Assignees: The University of Texas System Board of Regents, Austin, TX (US); The Texas A & M University System, College Station, TX (US)

( * ) Notice: Subject to any disclaimer, the term of this patent is extended or adjusted under 35 U.S.C. 154(b) by 215 days.

(21) Appl. No.: 10/390,343

(22) Filed: Mar. 17, 2003

(65) Prior Publication Data
US 2004/0053277 A1 Mar. 18, 2004

Related U.S. Application Data

(60) Provisional application No. 60/364,608, filed on Mar. 15, 2002.

(51) Int. Cl.
*C40B 30/00* (2006.01)

(52) U.S. Cl. ............................................ 506/7; 435/6

(58) Field of Classification Search ..................... None
See application file for complete search history.

(56) References Cited

U.S. PATENT DOCUMENTS

| 5,635,351 A | 6/1997 | Feuerstein et al. ............. 435/6 |
| 5,994,529 A | 11/1999 | Feuerstein et al. ....... 536/24.31 |
| 6,268,147 B1 * | 7/2001 | Beattie et al. ................. 435/6 |
| 6,492,118 B1 * | 12/2002 | Abrams et al. ................ 435/6 |

OTHER PUBLICATIONS

Fuller et al., Cancer Research 59:4228-4232 (1999).*
Rhee et al., Oncology Reports 6:393-401 (1999).*
Walker et al., Cancer Research 55(1): 20-23 (1999).*
Moch et al., Adv. Anat. Pathol. 8(1): 14-20 (2001).*
Sallinen et al., Cancer Research 60:6617-6622 (2000).*
Rickman et al., Cancer Research 61:6885-6891 (2001).*
Alizadeh et al., "Distinct types of diffuse large B-cell lymphoma identified by gene expression profiling," *Nature* 403 (6769), 503-511, 2000.
Ben-Dor et al., "Tissue classification with gene expression profiles" *J. Comput. Biol.* 7(3-4): 559-583, 2000.
Bittner et al., "Molecular classification of cutaneous malignant melanoma by gene expression profiling," *Nature* 406 (6795), 536-40, 2000.
Borg and Groenen, *In: Modern multidimensional scaling: Theory and applications*. Springer, New York. 1997.

Daumas-Duport et al., "Grading of astrocytomas: a simple and reproducible methods," *Cancer* 62, 2152-2165, 1988.
Devroye et al., *A Probablistic Theory of Pattern Recognition*, NY, Springer (Ed.), 1996.
Dougherty, "Small sample issues for microarray-based classification," *Comparative and Functional Genomics* 2:28-34, 2001.
Fuller et al., "Molecular classification of human diffuse gliomas by multidimensional scaling analysis of gene expression profiles parallels morphology-based classification, correlates with survival, and reveals clinically-relevant novel glioma subsets," *Brain Pathol.*, 12:108-116, 2002.
Fuller et al., "Reactivation of insulin-like growth factor binding protein 2 expression in glioblastoma multiforme: a revelation by parallel gene expression profiling," *Cancer Res.* 59:4228-4232, 1999.
Golub et al., "Molecular classification of cancer: class discovery and class prediction by gene expression monitoring," *Science* 286:531-537, 1999.
Hedenfalk et al., "Gene-expression profiles in hereditary breast cancer," *N. Engl. J. Med.*, 244: 539-548, 2001.
Kendall and Gibbons, *Rank Correlation Methods*, Fifth Edition. Oxford University Press, New York. 1990.
Khan et al., "Classification and diagnosis prediction of cancers using gene expression profiling and artificial neural networks," *Nature Medicine* 7(6):673-679, 2001.
Kim et al., "Identification of combination gene sets for glioma classification," *Mol. Cancer Therapeutics*, 1:1229-1236, 2002.
Kim et al., "Strong feature sets from small samples," *J. Comput. Biol.* 9(1):129-148, 2002.
Kleihues and Cavenee, *World Health Organization of Tumours of the Nervous System: Pathology and Genetics: Tumours of the nervous system,.* New York: Oxford University Press, 2000.
Perou et al., "Molecular portraits of human breast tumours," *Nature* 406 (6797), 747-752, 2000.
Sterling et al., *How to Build a Beowulf: A Guide to Implementation and Application of PC Clusters*, The MIT Press, Cambridge, Massachusetts. 1999.
Wang et al., "Tissue microarrays: applications in neuropathology research, diagnosis, and education," *Brain Pathol.*, 12:95-107, 2002.
Saxena et al., "Comparative molecular genetic profiles of anaplastic astrocytomas/glioblastomas multiforme and their subsequent recurrences," *Oncogene*, 18:1385-1390, 1999.

* cited by examiner

*Primary Examiner*—J. Douglas Schultz
*Assistant Examiner*—J. S. Lundgren
(74) *Attorney, Agent, or Firm*—Fulbright & Jaworski LLP

(57) ABSTRACT

The present invention provides a number of gene markers whose expression is altered in various gliomas. In particular, by examining the expression these markers, one can accurately classify a glioma as glioblastoma multiforme (GM), anaplastic astrocytoma (AA), anaplastic oligodendroglioma (AO) or oligodendroglioma (OL). The diagnosis may be performed on nucleic acids, for example, using a DNA microarray, or on protein, for example, using immunologic means. Also disclosed are methods of therapy.

19 Claims, 11 Drawing Sheets

GENE SETS FOR GLIOMA CLASSIFICATION

The present application claims priority to now abandoned U.S. Provisional Patent Application Ser. No. 60/364,608 filed on Mar. 15, 2002. The entire text of the above-referenced disclosure is specifically incorporated herein by reference without disclaimer.

BACKGROUND OF THE INVENTION

1. Field of the Invention

The present invention relates generally to the fields of molecular biology and oncology. More particularly, it concerns the classification of gliomas based on the expression of various proteins identified as relevant to various glioma states.

2. Description of Related Art

Gliomas are complex cancers with different growth characteristics and involves different types of cells. Because the original clone of tumor cells may exist at any stage during the cell differentiation, the boundaries between cell lineages can be blurred. The current morphologically-based tumor classifications often mix cell lineage features with tumor growth characteristics. The results are subjective and there can be disagreements among physicians as to what kind of tumor cell is involved. To date, a successful application of gene-based classification has not been applied to gliomas.

Molecular biology provides the potential for an improved method of tumor cell classification. This is based on the premise that all cell phenotypes have their origin in genetics. Thus, the rationale is that a detailed examination of gene expression will be the most accurate representation of a cell's character. Recent successes in the subclassification of neoplasms within a disease group using gene expression profiles provide support for such a belief (Golub et al., 1999; Alizadeh et al., 2000; Bittner et al., 2000).

Thus, the issue is how to best identify the "strong" feature genes that are closely linked to specific phenotypes from among the thousands of genes in gene expression profiles, and whether this information really aids classification of tumors more. There are many technical challenges in the path to accomplishing the task of finding the key links. Algorithms can assist in the identification of robust classifiers from very limited data sets. Three criteria have to be met: (a) given a set of variables, a classifier from the sample data should provide good classification over the general population; (b) the algorithm should be able to estimate the error of a designed classifier when data are limited; and (c) given a large set of potential variables, the algorithm should be able to select a set of variables as inputs to the classifier from the large number of expression level determinations provided by microarrays.

However, a major roadblock is the small sample size issue inherent to microarray-based classification efforts (Dougherty, 2001). Contributing to this are the limited numbers of human tissues for study and the cost of such gene expression profiling projects. Because classifiers are designed from observed expression vectors that have randomness arising from both biologic and experimental variability, the design, performance evaluation, and application of classifiers must take this randomness into account, especially when the number of samples (tissue specimens) is small, which is the case in most human tissue-based microarray experiments.

SUMMARY OF THE INVENTION

As discussed herein, the present invention provides, for the first time, a molecular basis for the classification of gliomas. This classification is based on the identification of genes and correlation of expresssion of these genes with various glioma states. Thus, in a particular embodiment, the present invention provides a method of classifying a glioma comprising (a) obtaining a tumor sample; (b) obtaining from cells of the tumor sample information on the expression of MAPKK1, HTF4, transducin β2, BMP2A, TrkB, DAP3, RAB3A, transcription elongation factor SII, integrin beta I, IGFBP2, NKEFB, HSP27, neuromodulin, and LIMK1; (c) comparing expression information obtained in step (b) with the expression information of at least a first known glioma cell type; and (d) classifying the tumor sample as glioblastome multiforme (GM), anaplastic astrocytoma (AA), anaplastic oligodendroglioma (AO) or oligodendroglioma (OL).

The tumor tissue sample may be from a needle biopsy, a resected tumor or a tumor fragment and the expression information obtained from the tumor sample in step (b) above, may be compared with at least a second or at least a third, or four known glioma cell types.

It is further contemplated that the expression information obtained in step (b) above, may be compared with a database of expression information obtained from a plurality of distinct samples each representing the first or four known glioma cell type(s), or any number of glioma cell types.

In some embodiments of the present invention a decision regarding the treatment of the subject from which the tumor sample was obtained is made. In further embodiments the invention comprise making a prediction on the efficacy of treating the subject from which the tumor sample was obtained and/or making a prediction on the survival of the subject from which the tumor sample was obtained.

The expression information obtained from the tumor sample may be determined by microarray analysis of transcripts, or by multiplex PCR of transcripts, or by immunohistochemistry. Such microarray analysis may comprise the use of oligonucleotides that hybridize to transcripts or cDNAs for the selected genes, wherein the oligonucleotides are disposed on the surface of a chip or wafer. The oligonucleotides may be about 25 to about 50 base pairs in length.

In some embodiments, the present invention may comprise obtaining information on the expression of transducin β1 from cells of the tumor sample. In further embodiments, the present invention comprise obtaining information on the expression of one or more of GRB2, TIE-2, TNFSF5, and CREB1 genes from cells of the tumor sample. It is further contemplated that the expression information of one or more of MUC18, RXR-β, clusterin, erythropoietin receptor, BCL-W, CDK7, myc, CC chemokine receptor, JAK3, DNase X, GNA13, RAB5A, PKA C-α, DNA ligase IV, acidic fibroblast growth factor and preprotachykinin β may be obtained from cells of the tumor sample. In still a further embodiment, the present invention comprise obtaining from cells of the tumor sample information on the expression of one or more of RAB3A, IL2R-γ, cyclin E, MAP kinase 10, BCL2A1, VEGFR2, CD1 B, thymosin β10, and U-PAR.

A chip or wafer comprising a nucleic acid microarray, wherein the nucleic acids hybridize to target transcripts from prostaglandin E2 receptor EP4 subtype, ephrin type A receptor 1, UV excision repair protein RAD23 homolog A, cytsteine protease ICE-LAP3, C/EBP homologous protein, RNA polymerase II elongation factor SIII p15 subunit, CD43 antigen, GP34, bone morphogenetic protein 1, and interleukin-2 is contemplated in the present invention.

The chip may be comprised of polymers, plastics, resins, polysaccharides, silica or silica-based materials, carbon, metals, inorganic glasses, or nitrocellulose. The chip or wafer may comprise nucleic acids such as cDNAs or oligonucleotides, and the oligonucleotides may be about 25 to about 50 base pairs or less in length.

The present invention further contemplates a chip comprising a nucleic acid microarray, wherein the nucleic acids hybridize to target transcripts from MAPKK1, HTF4, transducin β2, BMP2A, TrkB, DAP3, RAB3A, transcription elongation factor SII, integrin beta I, IGFBP2, NKEFB, HSP27, neuromodulin, and LIMK1. The nucleic acid microarray of which the chip or wafer comprises may further comprise one or more nucleic acids that hybridize to a target transcript from transducin β1; or one or more nucleic acids that hybridize to a target transcript selected from GRB2, TIE-2, TNFSF5, and CREB1; or one or more nucleic acids hybridize to a target transcript selected from MUC18, RXR-β, clusterin, erythropoietin receptor, BCL-W, CDK7, myc, CC chemokine receptor, JAK3, DNase X, GNA13, RAB5A, PKA C-α, DNA ligase IV, acidic fibroblast growth factor and preprotachykinin β; or one or more nucleic acids hybridize to a target transcript from RAB3A, IL2R-γ, cyclin E, MAP kinase 10, BCL2A1, VEGFR2, CD11B, thymosin β10, and uPAR.

In another particular embodiment, the present invention provides a method for predicting the survival of a patient with glioblastoma multiforme comprising (a) obtaining a tumor sample from said patient; (b) obtaining from cells of the tumor sample information on the expression of prostaglandin E2 receptor EP4 subtype, ephrin type A receptor 1, UV excision repair protein RAD23 homolog A, cytsteine protease ICE-LAP3, C/EBP homologous protein, RNA polymerase II elongation factor SIII p15 subunit, CD43 antigen, GP34, bone morphogenetic protein 1, and interleukin-2; and (c) making a prediction on the survival of the subject based on the expression information of the genes in step (b).

Microarray analysis may comprise the use of oligonucleotides that hybridize to transcripts or cDNAs for the selected genes, and wherein the oligonucleotides are disposed on the surface of a chip or wafer. The chip may be comprised of polymers, plastics, resins, polysaccharides, silica or silica-based materials, carbon, metals, inorganic glasses, or nitrocellulose.

In a further particular embodiment, the present invention provides a method of classifying a glioma comprising (a) obtaining a tumor sample; (b) obtaining from cells of the tumor sample information on the expression of one or more of the following gene combinations: Follitropin receptor and Thymosin β10; Cyclin D3 and SMARCA4; MRP and HSP70.1; MUC18, Clusterin and TNFSF5; MUC18, Transducin β1 and GRB2; MUC18, Transducin β1 and RXR-β; MUC18, Transducin β1 and Clusterin; MUC18, BCL-W and GRB2; MUC18, Transducin α1 and α1 catenin; MAP kinase 10, SMARCA4 and Neuronal aceytlcholine receptor α3; MUC18, GRB2 and Erythropoietin receptor; Clusterin, ISGF3γ and Erythropoietin receptor; TIE-2 and TNFSF5; IGFBP2 and EPHA1; IGFBP2 and CDK7; IGFBP2 and TNFSF5; Myc, IGFBP2 and CDK7; IGFBP2, TNSFS5 and CC chemokine receptor type 2; TIE-2, CXC chemokine receptor type 4 and EPHA1; TIE-2, CDK7 and JAK3; TIE-2, IGFBP2 and JAK3; TNFSF5 and DNase X; Prostaglandin E2 receptor E4 and DNase X; Prostaglandin E2 receptor E4 and TNFSF5; GNA13 and TNFSF5; ErbB4 and Prostaglandin E2 receptor E4; PKA C-α, TNFSF5 and Preprotachykinin β; DNase X, RκB DNA-binding and Preprotachykinin β; PKA C-α, DNA ligase IV and TNFSF5; DNA ligase IV, TNFSF5 and Acidic fibroblast growth factor; CREB1 and BCL2A1; CREB1, BCL2A1 and CD11B; CREB1, VEGFR2 and Thymosin β10; CREB1, VEGFR2 and CD11B antigen; CREB1, cyclin E and Thymosin β10; CREB1, BCL2A1 and Ednothelin receptor type A; U-PAR, CREB1 and VEGFR2; P55-FGR, Cyclin E and CREB1; CREB1, BCL2A1 and IL-12α; CREB1, VEGFR2 and Caspase 3; and CREB1, VEGFR2 and SCYB5; and (c) comparing expression information obtained in step (b) with the expression information of at least a first known glioma cell type; and (d) classifying the tumor sample as glioblastome multiforme (GM), anaplastic astrocytoma (AA), anaplastic oligodendroglioma (AO) or oligodendroglioma (OL).

It is further contemplated that combinations of two, three, four, five, ten, fifteen, twenty genes may be examined. In further embodiments it is contemplated that all combinations may be examined. The inventors further contemplate that a particular gene, such as listed in table 9, that discriminate OL from other gliomas, may be combined with one or more of the specific genes listed in table 9. Similarily, the inventors contemplate that a particular gene, such as listed in table 10, that discriminate GM from other gliomas, may be combined with one or more of the specific genes listed in table 10. It is further contemplated that a particular gene, such as listed in table 11, that discriminate AO from other gliomas, may be combined with one or more of the specific genes listed in table 11. In a further embodiment, a particular gene, such as listed in table 12, that discriminate AA from other gliomas, may be combined with one or more of the specific genes listed in table 12.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A—Transducin β itself could distinguish the OL (black) tissues from the others by being relatively low expressed in the OL tissues. The linear classifier is constructed after Gaussian spreading of samples with standard deviation σ of 0.7 which is shown as dotted circular bounds, and shown as a black vertical line. Also, transducin β and transcription elongation factor SII are found as the best combination of two genes to distinguish the AO tissues from others when the two AO/GM tissues are assigned to the AO class. No two genes could classify all tissues correctly. FIG. 1B—MAPKK1 and BMP2A are used to distinguish AA from OL/AO/GM with a linear discriminant. The AA tissues show high expression of either MAPKK1 or BMP2A while the others show relatively low expression in both genes. FIG. 1C—DAP3, transcription elongation factor SII, and integrin beta could distinguish the AO (green) and the AO/GM tissues from the others with misclassification error of 3.4% with Gaussian spreading with σ=0.7. Spreading is not shown to avoid messy graphics. An interesting part of this classifier is that none of these three genes is a part of strong features that are found by collectively considering the misclassification errors of all classifiers. Reasoning is that no gene has strong influence on discriminating both the AO and the AO/GM tissues from the others but more than a few need to collaborate, or AO and AO/GM are not in the same class at all, at least at gene expression level.

In FIG. 2A, all 597 genes are used to produce the MDS plot. Kendall's τ coefficient is used as a proximity measure. The plot shows the feasibility of separation of classes. In FIG. 2B, only 14 strong genes found in the analysis are used for the MDS plot. It is similar to a except inverted. It is quite clear that only 14 genes found in the analysis sustain the same discriminating power as all genes, and hence validate the usefulness of the method proposed in the paper. Using a smaller number of features also has an advantage as it decreases the amount of samples necessary to design a linear classifier. To test whether this clustering is spurious, the same experiments were performed using 14 randomly chosen genes and no visible clustering was found to occur (results not shown).

FIG. 4A—shown is a linear classifier derived solely from the sample points. FIGS. 4B-4D—shown are synthetic samples constructed from the original sample points by randomly adding noise of increasing variance to the original points to form larger samples that are spread about the original sample. Dotted circles are shown to represent a SD of spreading. A linear classifier has been derived for each synthetic sample. Increasing the variance increases the error. This method is called a Monte-Carlo simulation, but this simulation method is not used in the new method proposed. A new analytical method is developed to speed up the algorithm.

FIG. 5A—a strong multivariate (three-gene) discriminator of OL from other types of glioma. OL shows relatively low expression in all three genes. FIG. 5B—discriminator of GM from other types. GM shows relatively high expression of all three genes shown. FIG. 5C—discriminator of AO from others. FIG. 5D—discriminator of AA from others. Note that there is a clear separation between AO and others even though the hyperplane doesn't discriminate them perfectly. This is because of the nature of the algorithm. The algorithm tries to find the best discriminator that is efficient not only on the data set given but also on prediction. This is confirmed when LOO error is computed. The LOO error for the feature set and the data are not 0 but 0.04 (1 of 25). This is important because it again shows that the designed classifier does not over-fit the data. Scale on each axis represents a log2-transformed normalized intensity, log2 (intensity/median intensity of an array).

DESCRIPTION OF ILLUSTRATIVE EMBODIMENTS

Figure 1A:
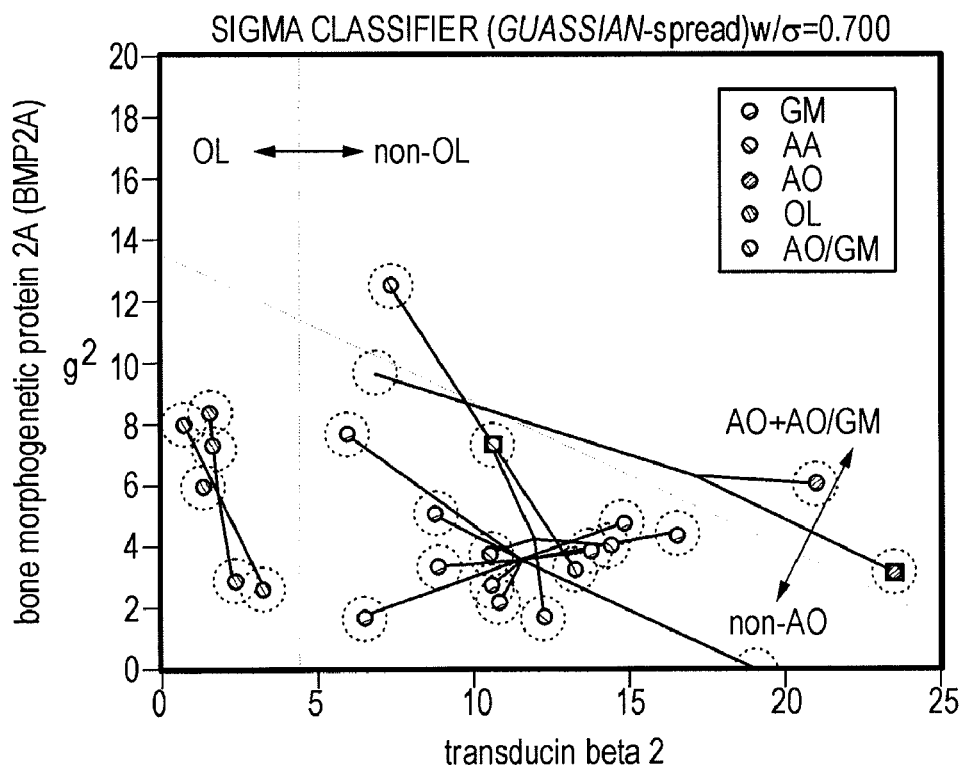
FIGS. 1A-1C.

Gliomas are the most common malignant primary brain tumors. These tumors are derived from neuroepithelial cells and can be divided into two principal lineages: astrocytomas and oligodendrogliomas. Current glioma classification schemes are based on morphologic feature assessment and remain highly subjective and problematic. Diagnoses are often dependent on the relative weighting of specific morphologic features by individual pathologists.

The inventors now have employed a recently proposed algorithm to identify strong gene feature sets that are responsible for distinct patient groups (Kim et al., 2002). This algorithm builds classifiers from a probability distribution resulting from spreading the mass of the sample points to make the classification more difficult, while maintaining sample geometry. In an effort to improve the accuracy of histologic diagnosis in patients with gliomas, the inventors applied this method to glioma tissue specimens from 25 patients with four different types of glioma: glioblastoma multiforme (GM), anaplastic astrocytoma (AA), anaplastic oligodendroglioma (AO), and low-grade oligodendroglioma (OL). After finding the sets of genes that are capable of accurately classifying the different types of glioma, they also identified strong features (genes) that are seemingly responsible for the distinct phenotype of each type of cancer.

As an example of how the present invention provides a significant advance, the tumor tissues from two patients participating in these studies exhibited ambiguous morphologic features and could be classified as either GM or AO using standard classification schemes. Depending on whether the two cases were grouped with AO or GM, different strong feature gene lists were generated. However, application of a classifier bank, capable of distinguishing all four groups of gliomas based on one set of criteria, was able to reliably discriminate the ambiguous samples. In a second aspect, the present invention has identified a group of genes which can provide a prognostic indicator of which patients afflicted with glioblastoma multiforme will have longer versus shorter survival times. Various aspects of the invention are described in detail below.

I. Gliomas

Gliomas are a diverse group of brain tumors that arise from the normal "glial" cells of the brain. The most important determinant of survival for gliomas is the "grade" of the glioma. The low-grade gliomas have a protracted natural history, while the high grade gliomas (anaplastic astrocytoma and glioblastoma multiforme) are much more difficult to successfully treat. The gliomas have specific signs and symptoms that are primarily related to the location of the glioma.

The temporal lobe gliomas, for example, may cause epilepsy, difficulty with speech or loss of memory. The frontal lobe gliomas may cause behavioral changes, weakness of the arms or legs or difficulty with speech. The occipital gliomas may cause loss of vision. The parietal gliomas may cause loss of spatial orientation, diminished sensation on the opposite side of the body, or inability to recognize once familiar objects or persons.

Surgery. The role of surgical resection in the treatment of malignant gliomas remains controversial even after 75 years of experience with primary malignant gliomas. Surgery permits a pathologic diagnosis to be established while the patient is still alive. However, many physicians argue that current radiologic imaging methods, including computed tomography (CT) and magnetic resonance imaging (MRI), permit a malignant brain tumor to be diagnosed without the necessity for attempted tumor resection and, thus, avoid the risks of surgery.

There is evidence that surgical reduction of tumor to very small residual amounts can prolong survival and permit patients to return to active lives. However, retrospective studies are subject to the criticism that the extent of attempted resection depends on the condition of the patient at the time of surgery (age, tumor location, clinical state), and that favorable conditions usually lead the surgeon to attempt a greater resection. Therefore, in such studies, it is not clear that the extent of surgery is as important to survival as are the more favorable prognostic variables. Nevertheless, these results support the surgical removal of the largest possible tumor volume that can be done safely. Patients are frequently able to return to a full, active life without the need for large doses of corticosteroids to ameliorate incapacitating symptoms.

Radiation. The proper portals and doses of radiation for brain tumors have changed with the advent of better imaging techniques. It has been reported in controlled studies that postoperative whole-brain radiation therapy increases patient survival over surgery alone. Other data showed that patients receiving 5,500 to 6,000 cGy of radiation live significantly longer than those receiving 5,000 cGy.

Prolonged survival has been reported in patients with recurrent malignant gliomas who were treated with temporarily implanted $I^{125}$ sources. A phase III trial randomized newly diagnosed patients to receive either (a) postoperative temporary $I^{125}$ seed implantation in the residual tumor bed, followed by standard external-beam radiotherapy plus IV BCNU; or (b) external radiotherapy plus BCNU, without seed implantation. Preliminary review of the results demonstrated that patients who received $I^{125}$ seeds lived longer than those who did not receive seeds, although the difference did not quite reach statistical significance. The study suggests but does not prove that brachytherapy extends survival beyond that achievable with external radiotherapy alone.

Radiosurgery. Radiosurgery, either by gamma knife or linear accelerator, has been shown to be effective in the treatment of arteriovenous malformations, small primary and metastatic brain tumors, and benign brain tumors, such as meningiomas and acoustic neuromas. Its investigational use in the treatment of gliomas has been addressed in several reports. In one trial, 37 patients received radiosurgery (1,000 to 2,000 cGy) to residual contrast-enhancing tumor after treatment with conventional external-beam radiation therapy. Local recurrence still occurred, but overall survival time may have been prolonged. Of the 37 patients, 7 (19%) required reoperation at a median time of 5 months after radiosurgery to remove necrotic tumor.

A major problem with radiosurgery (as with brachytherapy) is bias in the selection of patients for treatment. However, radiosurgery may be of benefit in a small group of good-prognosis patients with small tumors.

Chemotherapy. In 1983, it was reported that surgery plus radiation therapy and BCNU chemotherapy significantly adds to the survival of patients with malignant glioma, as compared with surgery plus radiation therapy without chemotherapy. High-dose methylprednisolone does not prolong survival. Both procarbazine and streptozotocin have demonstrated effectiveness similar to that of BCNU. BCNU alone is as effective as BCNU followed by procarbazine, or BCNU plus hydroxyurea followed by procarbazine plus teniposide. Methotrexate also has been reported to be effective in treating gliomas.

Intra-arterial BCNU is no more effective than intravenous BCNU and substantially more toxic. Serious toxicity induced by intra-arterial BCNU included irreversible encephalopathy and/or visual loss ipsilateral to the infused carotid artery. In the same study, fluorouracil did not influence survival. Neuropathologically, intra-arterial BCNU produced white matter necrosis. Intra-arterial cisplatinum is safer than BCNU administered by the same route but is no more effective than another nitrosourea, PCNU.

Over the past several years, there has been increasing interest in the use of targeted interstitial drug delivery using biodegradable microspheres and wafers. In a multicenter controlled trial, 222 patients with recurrent malignant gliomas who required reoperation were randomly assigned to receive surgically implanted biodegradable polymer discs containing 3.85% of BCNU or discs containing placebo. Median survival of the 110 patients who received BCNU polymers was significantly longer than that of the 112 patients who received placebo polymers (31 versus 23 weeks).

In addition to these controlled survival-based clinical trials, a large number of agents have also been tested in response-based studies in glioma patients. To date, however, no drug has been found to be more effective than the nitrosoureas. The combination of procarbazine, CCNU, and vincristine (PCV) has become a popular chemotherapeutic regimen for malignant glioma, and may be more effective than BCNU alone.

1. Glioblastoma Multiforme

Glioma-glioblastoma multiforme (GBM) is the most malignant of the neuroepithelial neoplasms, characterized by cellular pleomorphism, numerous mitotic figures, and often multinucleated giant cell. Proliferation of the vascular endothelium is seen as well as areas of necrosis with circumjacent pseudopalisading of the neoplastic cells. It can appear as either a well-circumscribed globular mass or a more diffuse mass lesion. The cut surface reveals necrosis, fatty degeneration, and hemorrhage. Hemorrhages have been found in 40%, with necrosis in up to 52% of the cases. The tumor is usually solid, although cysts may be present. Rarely the tumor consists of a solitary cyst and mural nodule.

Grading according to degree of malignancy was first proposed in 1949. In this classification, astrocytomas and glioblastomas represent different grades of malignancy of the same tumor. Grade I tumors, typically slow growing, are characterized by most cells having normal characteristics, and few mitotic features. Endothelial proliferation is absent. Grade II tumors, previously designated "astroblastomas," are characterized by an increased number of cells with polymorphic nuclei in mitoses. There is no clear line of demarcation from normal tissue. Grade III tumors represent anaplastic astrocytomas and Grade IV tumors represent the typical glioblastoma multiforme, characterized by cellular pleomorphism, vascular proliferation, mitoses, and multinucleated giant cells.

Glioblastoma multiforme constitutes approximately 7% of childhood intracranial neoplasms. The overall male to female ratio in children is 3:2. In adults, glioblastomas are noted most frequently in the frontal lobe with the temporal lobe second in frequency. Childhood glioblastomas of the cerebral hemispheres are also located most often in the frontal lobe; with the second most frequent site being the parietal lobe. Primary glioblastoma of the spinal cord in childhood is rare.

Glioblastoma multiforme in children appears to have two characteristic courses, each of which is related to the location of the tumor. Glioblastomas of the brainstem, a more primitive part of the central nervous system, occur at a younger age and have a shorter mean survival relative to those of the cerebral hemispheres. Glioblastoma multiforme of the cerebral hemisphere, a more highly developed part of the central nervous system, is characterized by onset in older children (13 years) and by a longer mean survival.

Headache is the most common complaint and papilledema the most common physical finding in children with hemispheric glioblastoma. Seizures are noted in up to one third of the children. Survival rates in patients with glioblastoma multiforme is uniformly poor. In studies of children treated with surgery and intracranial radiation, only one third of the children are alive one year after diagnosis. Survival of children with glioblastoma multiforme of either of the cerebral hemispheres or the brainstem has significantly increased since the advent of dexamethasone therapy. Presently therapy consists of surgery plus combination chemotherapy.

In summary it can be said that glioblastoma multiforme behaves similarly in both children and adults. The course of intracranial glioblastomas in children is more rapidly fatal than that of other similarly situated gliomas in childhood. While the overall survival rate is very poor in patients with a glioblastoma multiforme, intensive chemotherapy with surgical resection does offer some hope in increasing survival time among children.

2. Astrocytoma

Astrocytomas are tumors that arise from brain cells called astrocytes. Gliomas originate from glial cells, most often astrocytes. Sometimes the terms "astrocytoma" and "glioma" are used interchangeably. Astrocytomas are of two main types—high-grade and low-grade. High-grade tumors grow rapidly and can easily spread through the brain. Low-grade astrocytomas are usually localized and grow slowly over a long period of time. High-grade tumors are much more aggressive and require very intense therapy. The majority of astrocytic tumors in children are low-grade, whereas the majority in adults are high-grade. These tumors can occur anywhere in the brain and spinal cord. Common sites in children are the cerebellum (the area just above the back of the neck), cerebral hemispheres (the top part of the brain), and the thalamus or hypothalamus (located in the center of the brain).

Astrocytomas account for the majority of pediatric brain tumors. About 700 children are diagnosed with low-grade astrocytomas each year. In children, about 90 percent of astrocytomas are low-grade; only about 10 percent are high-grade.

Clinical features and symptoms depend on the location of the tumor and the child's age. Patients with cerebellar tumors have symptoms that include headache, vomiting and unsteadiness in walking. Tumors in the cerebral hemispheres commonly present with seizures: occasionally there is weakness of the arms and legs. Tumors in the hypothalamus often present with visual problems, while thalamic tumors cause headaches and arm or leg weakness.

Complete surgical removal of the tumor (resection) is the best option for tumors in areas where this can be done without damaging the normal, surrounding brain. For low-grade astrocytomas that are completely removed, further therapy is usually not needed. If the surgeon cannot completely remove the tumor, chemotherapy or radiation therapy may be given. The choice of treatments depends on the age of the patient, tumor location; some patients may even be followed without treatment. Radiation therapy is used for older children and those whose tumors keep growing despite chemotherapy. About 90 percent of children with low-grade astrocytomas are alive five years from diagnosis.

High-grade astrocytomas can rarely be removed totally because they often affect large areas of the brain by the time symptoms are obvious. All patients with high-grade astrocytomas usually recieve chemotherapy regardless of age. Most, except the very youngest, also receive radiation therapy. Currently, the prognosis is poor in the group of patients. The subset of patients who have high-grade tumors that can be removed may have survival rates of 35 to 40 percent after postsurgical irradiation with chemotherapy. The survival of other patients is very poor.

Research efforts for the low-grade astrocytomas focus on developing chemotherapy regimens that control tumor growth with fewer side effects on other organs of the body. Because these tumors grow slowly, the strategy is to give less intensive chemotherapy over longer periods of time. For older children and those whose tumors progress despite chemotherapy, new radiation techniques are under study to deliver more localized therapy with minimal effects on the normal brain.

For high-grade tumors, new approaches include use of new chemotherapy drugs, and the potential option of high doses of chemotherapy. Investigational new approaches, including new chemotherapy drugs and gene therapy to help protect the bone marrow from the side effects so that more intensive chemotherapy can be given are in various stages of development.

3. Oligodendroglioma and Anaplastic Oliogodendroglioma

Oligodendrogliomas are believed to be tumors of cells called oligodendrocytes that have a role in the structure and function of the brain. However, the origins of these tumor cells has been questioned. Oligodendrogliomas are classified as low grade oligodendroglioma (less aggressive) and anaplastic oligodendroglioma (more aggressive). More common that pure oligodendrogliomas are low grade and anaplastic tumors that are a mixture of astrocytoma and oligodendroglioma ("oligoastrocytomas").

The initial treatment of low grade oligodendroglioma and oligoastrocytoma consists of maximal surgery. The role of radiation therapy has been disputed, but younger people with minimal residual disease after surgery may have radiation therapy deferred as long as there is adequate monitoring of the tumor by MRI or CT scanning.

Anaplastic oligodendrogliomas and mixed oligoastrocytomas are more sensitive to chemotherapy than astrocytomas. A high rate of response to the use of PCV (procarbazine, CCNU, vincristine) chemotherapy has made the use of chemotherapy prior to radiation therapy the standard of care for these tumors. The actual effectiveness of this treatment regimen is currently being investigated in a large multinational trial.

Additionally, low grade oligodendrogliomas are also sensitive to chemotherapy, and PCV can be used when low grade tumors begin to grow despite prior radiation therapy.

II. Glioma-Related Genes and their Classification

As discussed above, the present invention provides, for the first time, a molecular basis for the classification of gliomas. This classification is based on the identification of genes, the expression of which correlates with the various glioma disease states (see Examples 1-3). The results are summarized in Tables 3-6. From these data, the inventors have selected the following set of genes (also Table 3) that are differentially regulated in various forms of glioma and, as a group, permit the accurate classification of each type of glioma: transducin beta 2, MAPKK1, BMP2A, HTF4, TrkB, RAB3A, DAP3, transcription elongation factor SII, integrin beta 1, IGFBP2, NKEFB, HSP27, neuromodulin and LIMK1. Using information derived from these fourteen gene targets, one can identify a glioma as either an oliogodendroglioma, an anaplastic oligodendroglioma, an anaplastic astrocytoma and glioblastoma multiforme. Additional genes may be added that assist in distinguishing the different forms of glioma, which are described in Tables 4-6.

III. Prognostic Determinations in Glioblastoma Multiforme

In addition to the glioma classification methods described above, the present invention also provides for making predictions on the clinical prospects of a patient with glioblastoma multiforme. Again, the inventors have used statistical analysis of gene expression data to select the following set of genes that are differentially regulated in various forms of glioma and, as a group, permit the accurate classification of each type of glioma: prostaglandin E2 receptor EP4 subtype, ephrin type A receptor 1, UV excision repair protein RAD23 homolog A, cytseine protease ICE-LAP3, C/EBP homologous protein, RNA polymerase II elongation factor SIII p15 subunit, CD43 antigen, GP34, bone morphogenetic protein 1, and interleukin-2. Using information derived from these ten gene targets, one can predict whether a glioblastoma multiforme patient will be a long term survivor or not.

IV. Methods of Assaying for Alterations in Gene Expression

Thus, in accordance with the present invention, methods are provided for the assaying of gene expression in patients suffering from gliomas. As discussed above, the principle applications of this assay are to: (a) determine what type of brain cancer a given patient suffers from; and (b) determine the likelihood of a glioblastoma multiforme patients survival. In each of these assays, the expression of a particular set of genes, set forth in the preceding sections, will be measured. The following is a discussion of various aspects of these methods.

1. Hybridization

There are a variety of ways by which one can assess gene expression. These methods either look at protein or at MRNA levels. Methods looking at mRNAs all fundamentally rely, at a basic level, on nucleic acid hybridization. Hybridization is defined as the ability of a nucleic acid to selectively form duplex molecules with complementary stretches of DNAs and/or RNAs. Depending on the application envisioned, one would employ varying conditions of hybridization to achieve varying degrees of selectivity of the probe or primers for the target sequence.

Typically, a probe or primer of between 13 and 100 nucleotides, preferably between 17 and 100 nucleotides in length up to 1-2 kilobases or more in length will allow the formation of a duplex molecule that is both stable and selective. Molecules having complementary sequences over contiguous stretches greater than 20 bases in length are generally preferred, to increase stability and selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, lower stringency conditions may be used. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

2. Amplification of Nucleic Acids

Since many nucleic acids, especially mRNAs, are in low abundance, nucleic acid amplification greatly enhances the ability to assess expression. The general concept is that nucleic acids can be amplified using paired primers flanking the region of interest. The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to selected genes are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemilluminescence, radioactive scintigraphy of incorporated radiolabel or fluorescent label or even via a system using electrical and/or thermal impulse signals.

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

A reverse transcriptase PCR™ amplification procedure may be performed to quantify the amount of mRNA amplified. Methods of reverse transcribing RNA into cDNA are well known (see Sambrook et al., 2000). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Whereas standard PCR usually uses one pair of primers to amplify a specific sequence, multiplex-PCR (MPCR) uses multiple pairs of primers to amplify many sequences simultaneously (Chamberlan et al., 1990). The presence of many PCR primers in a single tube could cause many problems, such as the increased formation of misprimed PCR products and "primer dimers", the amplification discrimination of longer DNA fragment and so on. Normally, MPCR buffers contain a Taq Polymerase additive, which decreases the competition among amplicons and the amplification discrimination of longer DNA fragment during MPCR. MPCR products can further be hybridized with gene-specific probe for verification. Theoretically, one should be able to use as many as primers as necessary. However, due to side effects (primer dimers, misprimed PCR products, etc.) caused during MPCR, there is a limit (less than 20) to the number of primers that can be used in a MPCR reaction. See also European Application No. 0 364 255 and Mueller & Wold (1989).

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2,202,328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicafive sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). European Application No. 329,822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; Ohara et al., 1989).

3. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 2000). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

4. Nucleic Acid Arrays

Microarrays comprise a plurality of polymeric molecules spatially distributed over, and stably associated with, the surface of a substantially planar substrate, e.g., biochips. Microarrays of polynucleotides have been developed and find use in a variety of applications, such as screening and DNA sequencing. One area in particular in which microarrays find use is in gene expression analysis.

In gene expression analysis with microarrays, an array of "probe" oligonucleotides is contacted with a nucleic acid sample of interest, i.e., target, such as polyA MRNA from a particular tissue type. Contact is carried out under hybridization conditions and unbound nucleic acid is then removed. The resultant pattern of hybridized nucleic acid provides information regarding the genetic profile of the sample tested. Methodologies of gene expression analysis on microarrays are capable of providing both qualitative and quantitative information.

A variety of different arrays which may be used are known in the art. The probe molecules of the arrays which are capable of sequence specific hybridization with target nucleic acid may be polynucleotides or hybridizing analogues or mimetics thereof, including: nucleic acids in which the phosphodiester linkage has been replaced with a substitute linkage, such as phophorothioate, methylimino, methylphosphonate, phosphoramidate, guanidine and the like; nucleic acids in which the ribose subunit has been substituted, e.g., hexose phosphodiester; peptide nucleic acids; and the like. The length of the probes will generally range from 10 to 1000 nts, where in some embodiments the probes will be oligonucleotides and usually range from 15 to 150 nts and more usually from 15 to 100 nts in length, and in other embodiments the probes will be longer, usually ranging in length from 150 to 1000 nts, where the polynucleotide probes may be single- or double-stranded, usually single-stranded, and may be PCR fragments amplified from cDNA.

The probe molecules on the surface of the substrates will correspond to selected genes being analyzed and be positioned on the array at a known location so that positive hybridization events may be correlated to expression of a particular gene in the physiological source from which the target nucleic acid sample is derived. The substrates with which the probe molecules are stably associated may be fabricated from a variety of materials, including plastics, ceramics, metals, gels, membranes, glasses, and the like. The arrays may be produced according to any convenient methodology, such as preforming the probes and then stably associating them with the surface of the support or growing the probes directly on the support. A number of different array configurations and methods for their production are known to those of skill in the art and disclosed in U.S. Pat. Nos. 5,445,934, 5,532,128, 5,556,752, 5,242,974, 5,384,261, 5,405,783, 5,412,087, 5,424,186, 5,429,807, 5,436,327, 5,472,672, 5,527,681, 5,529,756, 5,545,531, 5,554,501, 5,561,071, 5,571,639, 5,593,839, 5,599,695, 5,624,711, 5,658,734, 5,700,637, and 6,004,755.

Following hybridization, where non-hybridized labeled nucleic acid is capable of emitting a signal during the detection step, a washing step is employed where unhybridized labeled nucleic acid is removed from the support surface, generating a pattern of hybridized nucleic acid on the substrate surface. A variety of wash solutions and protocols for their use are known to those of skill in the art and may be used.

Where the label on the target nucleic acid is not directly detectable, one then contacts the array, now comprising bound target, with the other member(s) of the signal producing system that is being employed. For example, where the label on the target is biotin, one then contacts the array with a streptavidin-fluorescent conjugate under conditions sufficient for binding between the specific binding member pairs to occur. Following contact, any unbound members of the signal producing system will then be removed, e.g., by washing. The specific wash conditions employed will necessarily depend on the specific nature of the signal producing system that is employed, and will be known to those of skill in the art familiar with the particular signal producing system employed.

The resultant hybridization pattern(s) of labeled nucleic acids may be visualized or detected in a variety of ways, with the particular manner of detection being chosen based on the particular label of the nucleic acid, where representative detection means include scintillation counting, autoradiography, fluorescence measurement, calorimetric measurement, light emission measurement and the like.

Prior to detection or visualization, where one desires to reduce the potential for a mismatch hybridization event to generate a false positive signal on the pattern, the array of hybridized target/probe complexes may be treated with an endonuclease under conditions sufficient such that the endonuclease degrades single stranded, but not double stranded DNA. A variety of different endonucleases are known and may be used, where such nucleases include: mung bean nuclease, S1 nuclease, and the like. Where such treatment is employed in an assay in which the target nucleic acids are not labeled with a directly detectable label, e.g., in an assay with biotinylated target nucleic acids, the endonuclease treatment will generally be performed prior to contact of the array with the other member(s) of the signal producing system, e.g., fluorescent-streptavidin conjugate. Endonuclease treatment, as described above, ensures that only end-labeled target/probe complexes having a substantially complete hybridization at the 3' end of the probe are detected in the hybridization pattern.

Following hybridization and any washing step(s) and/or subsequent treatments, as described above, the resultant hybridization pattern is detected. In detecting or visualizing the hybridization pattern, the intensity or signal value of the label will be not only be detected but quantified, by which is meant that the signal from each spot of the hybridization will be measured and compared to a unit value corresponding the signal emitted by known number of end-labeled target nucleic acids to obtain a count or absolute value of the copy number of each end-labeled target that is hybridized to a particular spot on the array in the hybridization pattern.

V. Protein-Based Diagnostic Assays

In another aspects of the invention, one may employ a protein-based diagnostic approach. The most common form of protein identification is by the use of antibodies. As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting. The term "antibody" also refers to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies, both polyclonal and monoclonal, are also well known in the art (See, e.g., Antibodies: A Laboratory Manual, Cold Spring Harbor Laboratory, 1988; incorporated herein by reference).

In accordance with the present invention, immunodetection methods are provided. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle & Ben-Zeev O, 1999; Gulbis & Galand, 1993; De Jager et al., 1993; and Nakamura et al., 1987, each incorporated herein by reference.

In general, the immunobinding methods include obtaining a sample suspected of containing a relevant polypeptide, and contacting the sample with a first antibody under conditions effective to allow the formation of immunocomplexes. In terms of antigen detection, the biological sample analyzed may be any sample that is suspected of containing an antigen, such as, for example, a tissue section or specimen, a homogenized tissue extract, a cell, or even a biological fluid.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

As detailed above, immunoassays are in essence binding assays. Certain immunoassays are the various types of enzyme linked immunosorbent assays (ELISAs) and radioimmunoassays (RIA) known in the art. However, it will be readily appreciated that detection is not limited to such techniques, and Western blotting, dot blotting, FACS analyses, and the like may also be used.

In one exemplary ELISA, the antibodies of the invention are immobilized onto a selected surface exhibiting protein affinity, such as a well in a polystyrene microtiter plate. Then, a test composition suspected of containing the antigen, such as a clinical sample, is added to the wells. After binding and washing to remove non-specifically bound immune complexes, the bound antigen may be detected. Detection is generally achieved by the addition of another antibody that is linked to a detectable label. This type of ELISA is a simple "sandwich ELISA". Detection may also be achieved by the addition of a second antibody, followed by the addition of a third antibody that has binding affinity for the second antibody, with the third antibody being linked to a detectable label.

In another exemplary ELISA, the samples suspected of containing the antigen are immobilized onto the well surface and then contacted with the anti-ORF message and anti-ORF translated product antibodies of the invention. After binding and washing to remove non-specifically bound immune complexes, the bound anti-ORF message and anti-ORF translated product antibodies are detected. Where the initial anti-ORF message and anti-ORF translated product antibodies are linked to a detectable label, the immune complexes may be detected directly. Again, the immune complexes may be detected using a second antibody that has binding affinity for the first anti-ORF message and anti-ORF translated product antibody, with the second antibody being linked to a detectable label.

Another ELISA in which the antigens are immobilized, involves the use of antibody competition in the detection. In this ELISA, labeled antibodies against an antigen are added to the wells, allowed to bind, and detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background. The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

The antibodies of the present invention may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Brown et al., 1990; Abbondanzo et al., 1999; Allred et al., 1990).

Also contemplated in the present invention is the use of immunohistochemistry. This approach uses antibodies to detect and quantify antigens in intact tissue samples. Generally, frozen-sections are prepared by rehydrating frozen "pulverized" tissue at room temperature in phosphate buffered saline (PBS) in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and cutting up to 50 serial permanent sections.

VI. Gene Therapy

In another embodiment, the present invention provides for the administration of a gene therapy vector encoding one or more genes identified as being downregulated in gliomas. Alternatively, for genes that are overexpressed in gliomas, the transgenes may provide for reduced expression of appropriate targets. Various aspects of gene delivery and expression are set forth below.

1. Therapeutic Transgenes

Thus, in accordance with the present invention, there are provided methods of treating cancer utilizing genes identified as being overexpressed or underexpressed in gliomas. By inhibiting or increasing the expression of various of these genes, therapeutic benefit may be provided to patients.

2. Antisense

The term "antisense" nucleic acid refers to oligo- and polynucleotides complementary to bases sequences of a target DNA or RNA. When introduced into a cell, antisense molecules hybridize to a target nucleic acid and interfere with its transcription, transport, processing, splicing or translation. Targeting double-stranded DNA leads to triple helix formation; targeting RNA will lead to double helix formation.

Antisense constructs may be designed to bind to the promoter or other control regions, exons, introns or even exon-intron boundaries of a gene. Antisense RNA constructs, or DNA encoding such antisense RNA's, may be employed to inhibit gene transcription or translation within a host cell. Nucleic acid sequences which comprise "complementary nucleotides" are those which are capable of base-pairing according to the standard Watson-Crick complementarity rules. That is, that the larger purines will base pair with the smaller pyrimidines to form combinations of guanine paired with cytosine (G:C) and adenine paired with either thymine in the case of DNA (A:T), or uracil (A:U) in the case of RNA. Inclusion of less common bases such as inosine, 5-methylcytosine, 6-methyladenine, hypoxanthine and others in hybridizing sequences does not interfere with pairing.

As used herein, the terms "complementary" and "antisense sequences" mean nucleic acid sequences that are substantially complementary over their entire length and have very few base mismatches. For example, nucleic acid sequences of fifteen bases in length may be termed complementary when they have complementary nucleotides at thirteen or fourteen positions. Naturally, nucleic acid sequences with are "completely complementary" will be nucleic acid sequences which have perfect base pair matching with the target sequences, i.e., no mismatches. Other sequences with lower degrees of homology are contemplated. For example, an antisense construct with limited regions of high homology, but overall containing a lower degree (50% or less) total homology, may be used.

While all or part of the gene sequence may be employed in the context of antisense construction, statistically, any sequence of 17 bases long should occur only once in the human genome and, therefore, suffice to specify a unique target. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that oligonucleotides of 8, 9, 10, 11, 12, 13, 14, 15, 16, 17, 18, 19, 20 or more base pairs will be used. One can readily determine whether a given antisense nucleic acid is effective at targeting a gene simply by testing the construct in vitro to determine whether the gene's function or expression is affected.

In certain embodiments, one may wish to employ antisense constructs which include other elements, for example, those which include C-5 propyne pyrimidines. Oligonucleotides which contain C-5 propyne analogs of uridine and cytidine have been shown to bind RNA with high affinity and to be potent inhibitors or gene expression (Wagner et al., 1993).

3. Ribozymes

The term "ribozyme" refers to an RNA-based enzyme capable of targeting and cleaving particular DNA and RNA sequences. Ribozymes can either be targeted directly to cells, in the form of RNA oligonucleotides incorporating ribozyme sequences, or introduced into the cell as an expression construct encoding the desired ribozymal RNA. Ribozymes may be used and applied in much the same way as described for antisense nucleic acids. Ribozyme sequences also may be modified in much the same way as described for antisense nucleic acids. For example, one could include modified bases or modified phosphate backbones to improve stability or function.

4. Single Chain Antibodies

Naturally-occurring antibodies (of isotype IgG) produced by B cells, consist of four polypeptide chains. Two heavy chains (composed of four immunoglobulin domains) and two light chains (made up of two immunoglobulin domains) are held together by disulphide bonds. The bulk of the antibody complex is made up of constant immunoglobulin domains. These have a conserved amino acid sequence, and exhibit low variability. Different classes of constant regions in the stem of the antibody generate different isotypes of antibody with differing properties. The recognition properties of the antibody are carried by the variable regions (VH and VL) at the ends of the arms. Each variable domain contains three hypervariable regions known as complementarity determining regions, or CDRs. The CDRs come together in the final tertiary structure to form an antigen binding pocket. The human genome contains multiple fragments encoding portions of the variable domains in regions of the immunoglobulin gene cluster known as V, D and J. During B cell development these regions undergo recombination to generate a broad diversity of antibody affinities. As these B cell populations mature in the presence of a target antigen, hypermutation of the variable region takes place, with the B cells producing the most active antibodies being selected for further expansion in a process known as affinity maturation.

A major breakthrough was the generation of monoclonal antibodies, pure populations of antibodies with the same affinity. This was achieved by fusing B cells taken from immunized animals with myeloma cells. This generates a population of immortal hybridomas, from which the required clones can be selected. Monoclonal antibodies are very important research tools, and have been used in some therapies. However, they are very expensive and difficult to produce, and if used in a therapeutic context, can elicit and immune response which will destroy the antibody. This can be reduced in part by humanizing the antibody by grafting the CDRs from the parent monoclonal into the backbone of a human IgG antibody. It may be better to deliver antibodies by gene therapy, as this would hopefully provide a constant localized supply of antibody following a single dose of vector. The problems of vector design and delivery are dealt with elsewhere, but antibodies in their native form, consisting of two different polypeptide chains which need to be generated in approximately equal amounts and assembled correctly are not good candidates for gene therapy. However, it is possible to create a single polypeptide which can retain the antigen binding properties of a monoclonal antibody.

The variable regions from the heavy and light chains (VH and VL) are both approximately 110 amino acids long. They can be linked by a 15 amino acid linker (e.g., (glycine$_4$serine)$_3$), which has sufficient flexibility to allow the two domains to assemble a functional antigen binding pocket. Addition of various signal sequences allows the scFv to be targeted to different organelles within the cell, or to be secreted. Addition of the light chain constant region (Ck) allows dimerization via disulphide bonds, giving increased stability and avidity. However, there is evidence that scFvs spontaneously multimerize, with the extent of aggregation (presumably via exposed hydrophobic surfaces) being dependent on the length of the glycine-serine linker.

The variable regions for constructing the scFv are obtained as follows. Using a monoclonal antibody against the target of interest, it is a simple procedure to use RT-PCR to clone out the variable regions from MRNA extracted from the parent hybridoma. Degenerate primers targeted to the relatively invariant framework regions can be used. Expression constructs are available with convenient cloning sites for the insertion of the cloned variable regions.

5. Vectors

In accordance with the present invention, both stimulatory and inhibitory genes may be provided to a cancer cell and expressed therein. Stimulatory genes are generally simply copies of the gene of interest, although in some cases they may be genes, the expression of which direct the expression of the gene of interest. Inhibitory genes, discussed above, may include antisense or single-chain antibody genes.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1989 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

a. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, on the world wide web) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Table 1 lists non-limiting examples of elements/promoters that may be employed, in the context of the present invention, to regulate the expression of a RNA. Table 2 provides non-limiting examples of inducible elements, which are regions of a nucleic acid sequence that can be activated in response to a specific stimulus.

TABLE 1

Promoter and/or Enhancer

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-Dra | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Ornitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| γ-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsch et al., 1990 |
| $α_1$-Antitrypsin | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989 |

TABLE 1-continued

Promoter and/or Enhancer

| Promoter/Enhancer | References |
|---|---|
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 2

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | Poly(rI)x Poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor α | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Non-limiting examples of such regions include the human LIMK2 gene (Nomoto et al., 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki et al., 1998), D1A dopamine receptor gene (Lee et al., 1997), insulin-like growth factor II (Wu et al., 1997), and human platelet endothelial cell adhesion molecule-1. (Almendro et al., 1996).

b. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5'-methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

c. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

d. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference).

e. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

f. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

g. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

h. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

i. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, *E. coli* is often transformed using derivatives of pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as, for example, E. coli LE392.

Further useful plasmid vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, and the like.

Bacterial host cells, for example, E. coli, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

j. Viral Vectors

The ability of certain viruses to infect cells or enter cells via receptor-mediated endocytosis, and to integrate into host cell genome and express viral genes stably and efficiently have made them attractive candidates for the transfer of foreign nucleic acids into cells (e.g., mammalian cells). Non-limiting examples of virus vectors that may be used to deliver a nucleic acid of the present invention are described below.

(i). Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell-specific construct that has been cloned therein. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992).

(ii). AAV Vectors

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno-associated virus (AAV) is an attractive vector system as it has a high frequency of integration and it can infect non-dividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

(iii). Retroviral Vectors

Retroviruses have promise as gene delivery vectors due to their ability to integrate their genes into the host genome, transferring a large amount of foreign genetic material, infecting a broad spectrum of species and cell types and of being packaged in special cell-lines (Miller, 1992).

In order to construct a retroviral vector, a nucleic acid (e.g., one encoding gene of interest) is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

(iv). Other Viral Vectors

Other viral vectors may be employed as vaccine constructs in the present invention. Vectors derived from viruses such as vaccinia virus (Ridgeway, 1988; Baichwal and Sugden, 1986; Coupar et al, 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

(v). Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

6. Vector Delivery and Cell Transformation

Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by ex vivo transfection (Wilson et al., 1989, Nabel and Baltimore, 1987), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by Agrobacterium-mediated transformation (U.S. Pat. Nos. 5,591,616 and 5,563,055, each incorporated herein by reference); by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

a. Injection

In certain embodiments, a nucleic acid may be delivered to an organelle, a cell, a tissue or an organism via one or more injections (i.e., a needle injection), such as, for example, subcutaneously, intradermally, intramuscularly, intervenously, intraperitoneally, etc. Methods of injection of vaccines are well known to those of ordinary skill in the art (e.g., injection of a composition comprising a saline solution). Further embodiments of the present invention include the introduction of a nucleic acid by direct microinjection. Direct microinjection has been used to introduce nucleic acid constructs into *Xenopus* oocytes (Harland and Weintraub, 1985).

b. Electroporation

In certain embodiments of the present invention, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

c. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

d. DEAE-Dextran

In another embodiment, a nucleic acid is delivered into a cell using DEAE-dextran followed by polyethylene glycol. In this manner, reporter plasmids were introduced into mouse myeloma and erythroleukemia cells (Gopal, 1985).

e. Sonication Loading

Additional embodiments of the present invention include the introduction of a nucleic acid by direct sonic loading. LTK-fibroblasts have been transfected with the thymidine kinase gene by sonication loading (Fechheimer et al., 1987).

f. Liposome-Mediated Transfection

In a further embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen).

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991).

In yet further embodiments, a liposome may be complexed or employed in conjunction with both HVJ and HMG-1. In other embodiments, a delivery vehicle may comprise a ligand and a liposome.

g. Receptor Mediated Transfection

Still further, a nucleic acid may be delivered to a target cell via recepior-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present invention.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor-mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present invention can be specifically delivered into a target cell in a similar manner.

h. Microprojectile Bombardment

Microprojectile bombardment techniques can be used to introduce a nucleic acid into at least one, organelle, cell, tissue or organism (U.S. Pat. Nos. 5,550,318, 5,538,880, 5,610,042, and PCT Application WO 94/09699; each of which is incorporated herein by reference). This method depends on the ability to accelerate DNA-coated microprojectiles to a high velocity allowing them to pierce cell membranes and enter cells without killing them (Klein et al., 1987). There are a wide variety of microprojectile bombardment techniques known in the art, many of which are applicable to the invention.

In this microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into a cell (e.g., a plant cell) by acceleration is the Biolistics Particle Delivery System, which can be used to propel particles coated with DNA or cells through a screen, such as a stainless steel or Nytex screen, onto a filter surface covered with cells, such as for example, a monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

VII. Pharmaceutical Formulations and Routes of Administration

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Supplementary active ingredients also can be incorporated into the compositions.

Administration of these compositions according to the present invention will be via any common route so long as the target tissue is available via that route. This includes intradermal, subcutaneous, intramuscular, intraperitoneal or intravenous injection. In particular, intratumoral routes and sites local and regional to tumors are contemplated. Such compositions would normally be administered as pharmaceutically acceptable compositions, described supra.

The active compounds also may be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy administration by a syringe is possible. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

For oral administration the polypeptides of the present invention may be incorporated with excipients that may include water, binders, abrasives, flavoring agents, foaming agents, and humectants.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

VIII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Primary glioma tissues. All primary GM tissues were acquired from the Brain Tumor Center tissue bank of The University of Texas M. D. Anderson Cancer Center. The tumors were diagnosed according to two classifications: St. Anne-Mayo (Daumas-Duport et al., 1988) and the World Health Organization (Kleihues et al., 2000). Herein, gliomas are termed according to the St. Anne-Mayo nomenclature: low-grade OL, AO, AA, and GM. Tissue bank specimens were quick-frozen shortly after surgical removal and stored at −80° C. Hematoxylin-eosin (H&E)-stained frozen tissue sections are routinely prepared from all tissue bank specimens for screening. All tissue specimens for CDNA array analysis were screened by a neuropathologist (G.N.F.), and the diagnoses were independently confirmed by a second neuropathologist. The glioma tissue blocks were specifically selected for densest and purest tumor. All were comparatively and uniformly "pure" with minimal contamination by normal brain parenchyma and minimal variation between samples.

Isolation of total RNA and mRNA from tissues. Tissues were ground to powder under frozen conditions, and 0.3-1.5 g of tissue powder was lysed in TRI Reagent (Molecular Research Center, Cincinnati, Ohio). RNA was isolated as described previously (Fuller et al., 1999).

Hybridization to the human Atlas cDNA expression array blots. The cDNA microarray containing fragments representing 597 human genes with known functions and known tight transcriptional controls (Clontech Laboratories, Inc., Palo Alto, Calif.) was used for these experiments, as described previously (Fuller et al., 1999). After a high-stringency wash, the hybridization pattern was analyzed by autoradiography and quantified by phosphoimaging.

Development of an Algorithm for Finding Strong Feature (Gene) Sets. Classifiers that categorize sample tissues based on gene expression values were desired. Classifiers involving small numbers of genes were desired because (a) the limited number of samples often available in clinical studies makes classifier design and error estimation problematic for large feature sets (Dougherty, 2001); and (b) small gene sets facilitate design of practical immunohistochemical diagnostic panels. Thus, were use a simple classifier and a small number of genes (at most three in this study) to form classifiers (Kim et al., 2002).

Given a set of features on which to base a classifier, two issues must be addressed: (a) design of a classifier from sample data; and (b) estimation of its error. When selecting features from a large class of potential features, the key issue is whether a particular feature set provides good classification. A key concern is the precision with which the error of the designed classifier estimates the error of the optimal classifier. When data are limited, an error estimator may be unbiased but may have a large variance and therefore may often be low. This can produce many feature sets and classifiers with low error estimates. The algorithm used mitigates this problem by designing classifiers from a probability distribution resulting from spreading the mass of the sample points. The algorithm is parameterized by the variance of the distribution. The error gives a measure of the strength of the feature set as a function of the variance.

When the data are limited, and all of it is used to design the classifier, there are several ways to estimate the classifier error. The resubstitution estimate, $\epsilon_n$, for a sample of size n is the fraction of errors made by the designed classifier on the sample. Typically, it is low-biased, meaning $E[\epsilon_n] \leq E[\epsilon_n]$, the expected value of the actual error. For LOO estimation, n classifiers are designed from sample subsets formed by leaving out one data point at a time. Each is applied to the left-out point, and the estimator $\hat{\epsilon}_n$ is 1/n times the number of errors made by the n classifiers. It is an unbiased estimator of $\epsilon_{n-1}$, meaning that $E[\hat{\epsilon}n]=E[\epsilon_{n-1}]$. This unbiased comes at a cost: the variance of the LOO estimator is greater than that of resubstitution (Devroye et al., 1996).

For $\sigma \geq 0$, the algorithm constructs used from the sample data a linear classifier $\psi_\sigma$, where $\sigma^2$ gives the variance of the distribution used to spread the data. Both $\psi_\sigma$ and its error, $\epsilon_\sigma$, are computed analytically. For $\sigma=0$, which means there is no spreading of the sample mass, $\epsilon_\sigma$ is equal to the resubstitution error estimate for the sample. Thus, the standard theory informs us that the variance of $\epsilon_0$ is less than that of the LOO estimator. Moreover, model-based studies indicate that the variance of $\epsilon_\sigma$ decreases as $\sigma$ increases. To standardize the interpretation of the results, $\sigma$ is normalized relative to the variance of the data. Under this normalization, simulation studies with Gaussian distributions show $\epsilon_\sigma$ to be an unbiased estimator of the optimal linear classifier for $\sigma=0.4$ and to be increasingly high-biased for increasing $\sigma$. To obtain conservative estimates of the optimal error, $\sigma \geq 0.4$. Moreover, for very small feature sets, the maximum variance of the features was normalized. By being conservative, the chance that the resulting error estimate was reduced is optimistic. When considering a large number of potential feature sets in the presence of a small amount of data, the salient issue is one of data mining. Taking a conservative approach reduces the number of optimistic error estimates while at the same time selecting feature sets that perform well on a distribution that is significantly more dispersed than the actual data.

Multidimensional Scaling (MDS). Informally, the purpose of MDS is to provide a visual representation of the pattern of proximities among a set of objects, which in this case were glioma tissues. Since each tissue sample can be considered to be a 597-dimensional vector (there are 597 genes on each array), the proximity between any two samples using some numerical distance measure could be computed. Some common measures of proximity are the standard correlation coefficient and ordinal correlation coefficients, such as Spearman's $\rho$ or Kendall's $\tau$ (Kendall & Gibbons, 1990), and those based on norms, such as the Euclidean distance. MDS takes proximities between all pairs of tissues and arranges points in a low-dimensional Euclidean space (typically 2- or 3-dimensional), such that the tissues that are most similar correspond to points that are near each other in this space. Kendall's $\tau$ measure is used to minimize the effect of outliers on the similarity values, as it is well known that the classic linear correlation coefficient can be unduly influenced by outlying observations.

Example 2

Preliminary Results

Current glioma classifications are based on morphologic feature assessment and remain subjective and problematic. For example, among the 25 glioma cases in this study, two cases could be classified as either AO or GM depending on the morphologic criteria used, and are thus designated AO/GM. A primary goal of functional genomics is to identify key genes and gene combinations, small in number, that are potentially useful for diagnosis or as candidate therapeutic targets (Golub et al., 1999; Alizadeh et al., 2000; Bittner et al., 2000; Hedenfalk et al., 2001; Perou et al., 2000; Ben-Dor et al., 2000; Khan et al., 2001). A new algorithm (Kim et al., 2002) designed to find robust gene sets from small samples has been applied to the gene expression profile data derived from 25 human glioma surgical specimens. This algorithm builds classifiers from a probability distribution resulting from spreading the mass of the sample points to make the classification more difficult, while maintaining sample geometry (Kim et al., 2002).

The inventors have designed two-class linear classifiers, with at most three genes per classifier. The dispersion levels (amount of spread) of samples are varied from standard deviation $\sigma=0.6$ to $\sigma=0.9$, which according to the algorithm model give conservative error estimates. Classifiers that provide good classification at $\sigma$ in this range are "strong classifiers." Six classifications are considered: OL vs. others, AA vs. others, AO vs. others, and GM vs. others when AO/GM in AO, and AO vs. others when AO/GM in GM, and GM vs. others when AO/GM in GM.

Table 3 shows some gene sets with the smallest number of genes in each feature vector that provide strong classification. Errors are based on the algorithm model. From theoretical considerations and experience with the model, for $\sigma \geq 0.7$, errors below 4% are very small, and errors below 8% indicate decent classification.

As seen in Table 3 and in FIG. 1A, transducin β2, encoding a guanine nucleotide-binding protein, can by itself distinguish OL from others with a very small misclassification error (0.24%), as OL tissues express low levels of this molecule. A family member, transducin β1, is also expressed at low levels in OL tissues (Table 4). The low-grade nature of OL is consistent with the observation that the apoptosis-promoting genes, caspase 9 and caspase 10, are expressed at higher levels in OL tissues than in other gliomas.

Figure 1B:
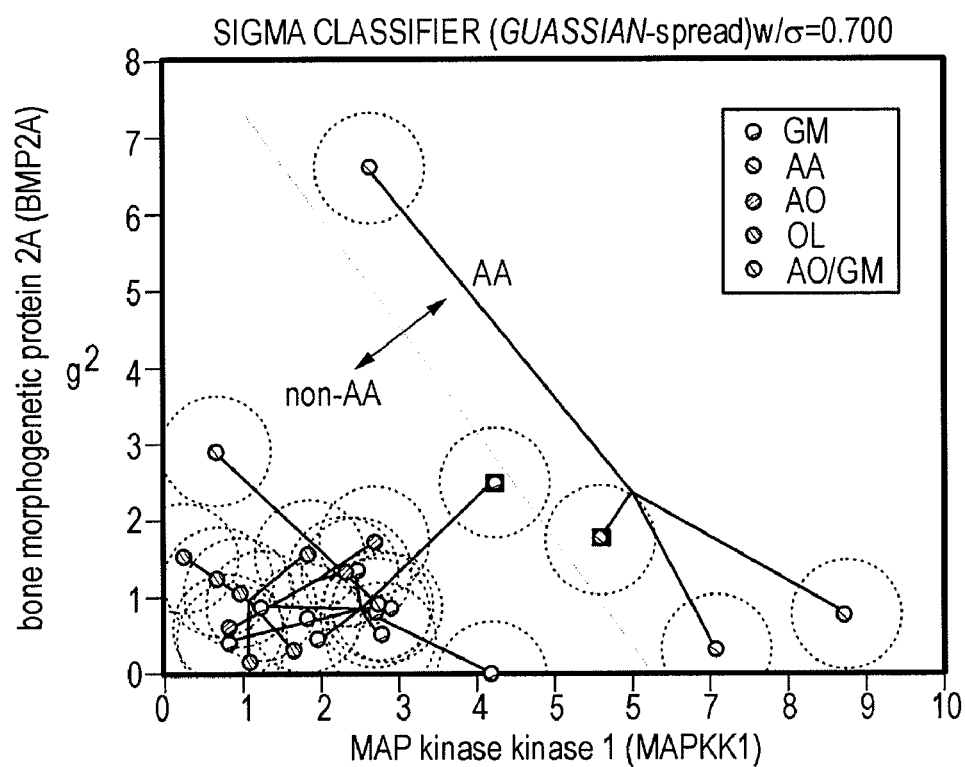

Numerous two-gene sets can distinguish AA from other tissues (Table 3). For example, using the two genes encoding mitogen-activated protein kinase kinase 1 (MAPKK) and bone morphogenetic protein 2A (BMP2A), for dispersion level $\sigma=0.7$, the model misclassification error is only 3.5% (See Table 3 and FIG. 1B). Table 4 lists some of the top-ranked genes associated with AA. Most of these genes are involved in cell proliferation and cell adhesion, and the levels of these genes are generally higher in AA than in the other gliomas.

Finding genes that distinguish AO from others or GM from others is more challenging because there are two tumor specimens with both AO and GM features. This ambiguity in histology-based classification reflects one example of the continuum nature of the disease and the need for a more refined classification based on molecular events. A particular advantage of our algorithm (Kim et al., 2002) is that it may help identify genes that are linked to subtle differences between the two indeterminant gliomas and AOs and GMs with unambiguous histologic features. The inventors assigned the two AO/GM tissues to AO in the first analysis and then to GM in the second analysis.

Figure 1C:
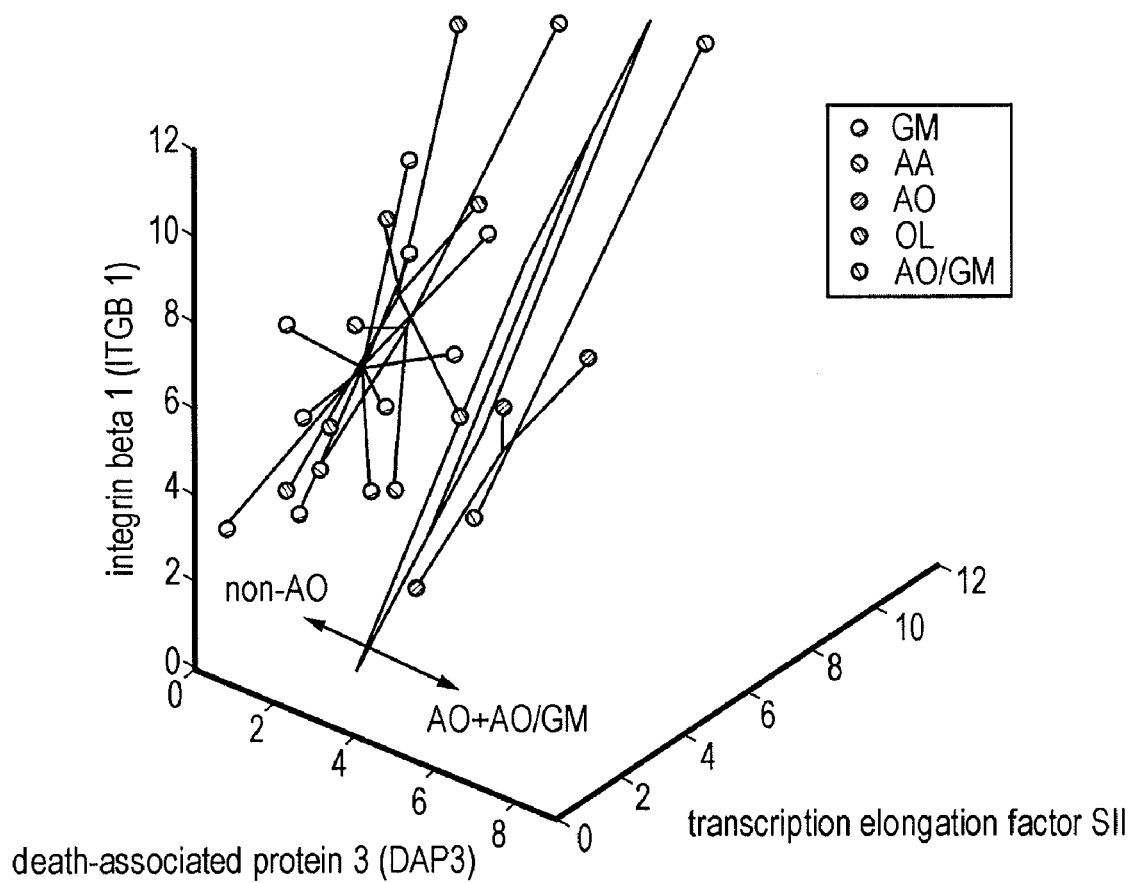

Consistent with the ambiguity in the histological classification, it is much more difficult to find linear classifiers that distinguish AO or GM from the others when the two AO/GM cases are assigned to either group. Even the best two-gene classifiers show high errors after spreading, and at least one case is misclassified on the sample data (FIG. 1A). Three genes can achieve better separation (FIG. 1C). Intriguingly, none of the three genes is among the strong features found by collectively considering the misclassification errors of all classifiers. This finding suggests that the AO/GM tumors may constitute a distinct group separate from both AO and GM. Although the inventors could attempt to find genes that distinguish the two AO/GM cases from others, the number of tissue samples in this group in the present study is too small to derive significant classifiers. Instead, the inventors have compared the strong feature gene lists resulting from the grouping of the AO/GM cases with either AO or GM.

These lists are informative. Table 5 lists the strong genes found to distinguish GM from others in either case. The sections list (a) genes found commonly in both cases; (b) genes found only when the AO/GM tissues are assigned to the AO class; and (c) genes found only when the AO/GM tissues were assigned to the GM class. As shown in Table 5C, several genes encoding proteins involved in vascularization—VEGF, semaphorin J, integrin 7B, VEGFc, and endothelin 3—are the top features for the GM group. These genes are not, however, strong features for GM when the AO/GMs are grouped with AO (Table 5B). This is consistent with prior knowledge regarding the shared features of the two AO/GM cases with GM—namely, extensive vascularization—and thus the association with genes linked to angiogenesis. Nonetheless, it is still possible that angiogenesis in these two groups has subtle differences. For example, the gene encoding angiopoietin 1 receptor, or TIE-2, is a strong feature gene (upregulated in GM) in both scenarios. This suggests that TIE-2 gene expression level in AO/GM cases is at the lower end of the expression spectrum for GMs, which is why moving the two cases into AO does not change the separation of GM from others. Similar genes with this phenomenon include those encoding IGFBP2, FGFR1, VEGFR, and p19-ink4. Thus, the two AO/GM cases represented a transition from typical AO to typical GM—they gained some strong features of GM but only minimally gained others. This is perhaps a molecular illustration of a disease in progression, and may offer a glimpse of gene hierarchy in the context of GM.

Similarly, comparison of the strong feature genes that distinguish AO from other gliomas when the AO/GMs are grouped with AO or GM should be informative about the gene hierarchy in AO. Some genes are likely involved in lineage determination. AO is a tumor of oligodendrocytes. Thus, the genes that define this lineage would likely disappear from the strong feature list if the two AO/GMs are treated as GMs (Table 6). In contrast, the genes that remain after the AO/GMs are grouped with GM may point to alterations in molecular events that occur during the transition from AO to GM. For example, bone morphogenesis protein 4, cyclin A1, and cyclin G2 remain strong features after AO/GM removal, suggesting that typical AOs have growth characteristics distinct from those of other gliomas and that those characteristics are altered during the transition of those tumors from AO to GM. Thus, searching for strong feature genes in combination with histological characteristics may provide deeper insight into the molecular events occurring during disease progression. At last, the average misclassification error rates are reported in the tables. They are simply, for each gene, arithmetic average of misclassification errors of those classifiers of which the gene is a member. The absolute numbers themselves do not mean too much, but it may be only useful for comparison, as a measure of strength of average classification power of each gene.

Having found several sets of two-class classifiers, the inventors can construct multi-class classifiers by combining two-class classifiers. The resulting classifier bank produces a four-element vector, with vectors 1000, 0100, 0010, and 0001 classifying the tissues as AA, AO, GM, and OL, respectively. It is possible that all elements are 0, indicating that the classifier cannot decide clearly to which class the tissue belongs. It is also possible that more than one element in the output vector is 1, indicating confusion between the two classes in the gene expression level. The combination of two- and three-gene classifiers in the classifier banks results in a gene set composed of all genes that occur in at least one of the classifiers in the bank. The set of 14 genes given in Table 3 is a promising classifier bank for the cases in this study. As the inventors tested all possible classifier banks constructed using the sets of genes shown in Table 3, they showed no misclassification errors in leave-one-out estimation, for the samples used in the study.

Figure 2A:
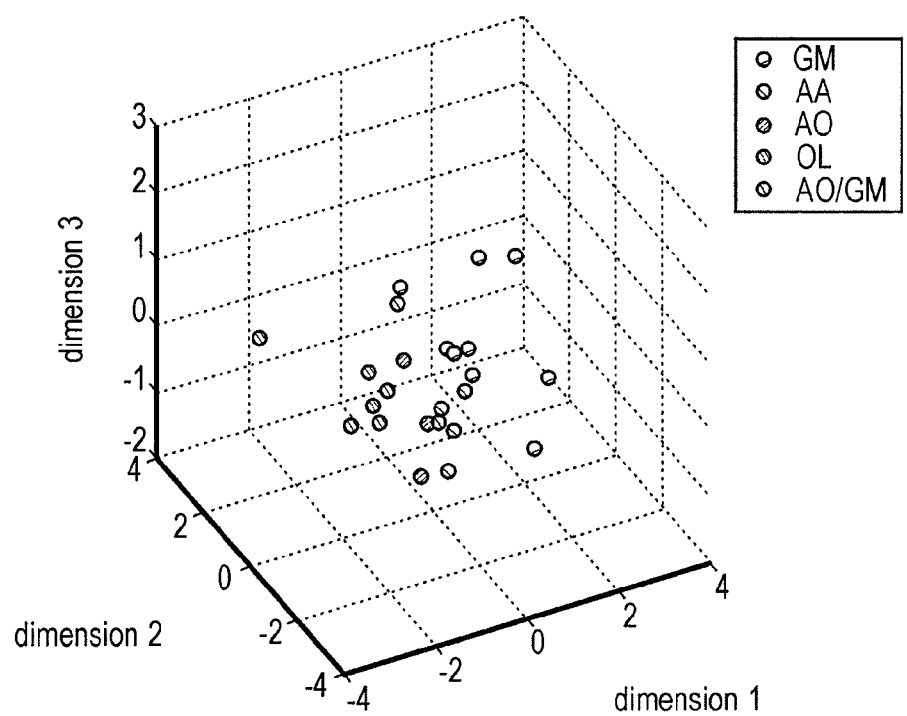
FIGS. 2A-2B. A Multidimensional Scaling plot is often used to observe the discrimination power of a feature set.
Figure 2B:
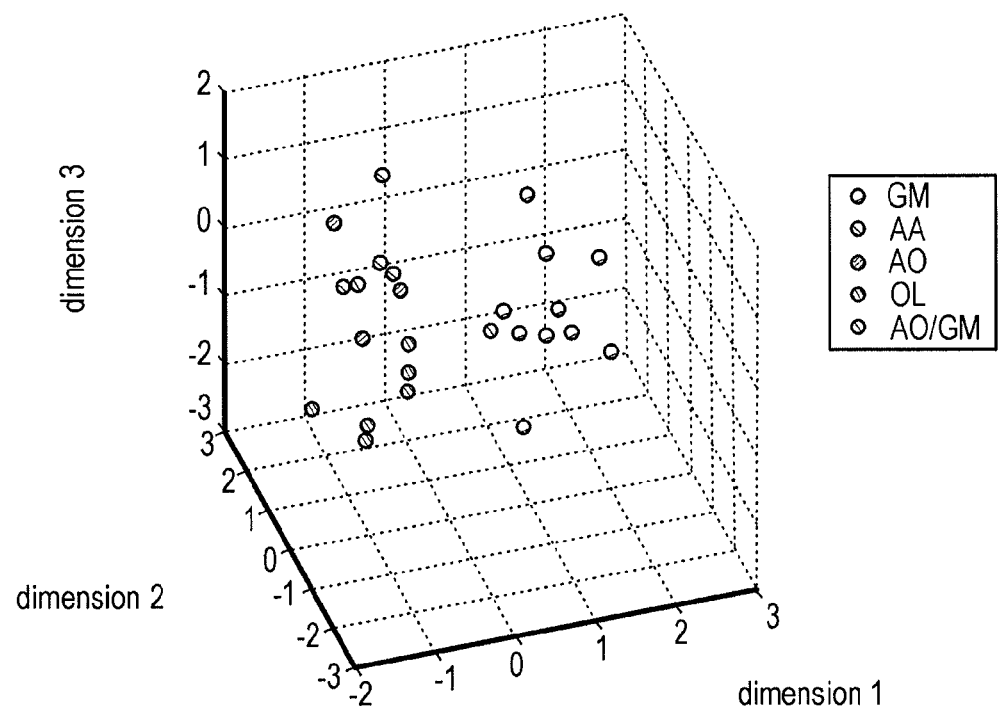

To investigate the potential discriminatory power of the 14 genes, the inventors constructed a Multidimensional Scaling (MDS) solution (Borg & Groenen, 1997) on the basis of these 14 genes and compared it with the solution constructed on the basis of all 597 genes. FIG. 2 shows the 3-dimensional MDS solution based on the 14 genes or on all 597 genes using Kendall's $\tau$ coefficient as the similarity measure. It can be seen that the 14 genes from the classifier bank are able to cluster the 25 tissue samples just as well as all 597 genes.

TABLE 3

Strong feature vectors to classify each class from others

| | Gene sets | | | Errors (%) |
|---|---|---|---|---|
| OL | Transducin β2 | | | 0.24 |
| AA | MAPKK1 | BMP2A | | 3.46 |
| | MAPKK1 | HTF4 | | 2.79 |
| AO | TrkB | RAB3A | DAP3 | 3.41 |
| | DAP3 | transcription elongation factor SII | Integrin beta 1 | 5.79 |
| GM | IGFBP2 | NKEFB | HSP27 | 0.04 |
| | IGFBP2 | NKEFB | Neuromodulin | 0.16 |
| | IGFBP2 | NKEFB | LIMK1 | 0.18 |

The two AO/GM tissues were assigned to AO class. For each class, each set of genes could perfectly classify samples used in the study, and showed very small misclassification errors on dispersed samples and large separations between the class and others. Indeed, the classifiers in Table 3 have no misclassification error on the sample data using leave-one-out error estimation. If one increases the number of genes in a feature vector, the number of sets increases proportionately. Classifiers (binary) constructed from these genes can be used to construct multi-class classifiers by putting them together as classifier banks. OL, oligodendroglioma; AA, anaplastic astrocytoma; AO, anaplastic oligodendroglioma; GM, glioblastoma multiforme.

TABLE 4

Strong Features Found for Oligodendroglioma & Anaplastic Astrocytoma

| | Error |
|---|---|
| (A) OL from the others | |
| Guanine nucleotide-binding protein G-i/G-s/G-t beta subunit 2; transducin beta 2 subunit 2 | 0.12% |
| caspase 10 (CASP10) | 1.44% |
| nuclear factor NF90 | 1.68% |
| Endothelin receptor type B (EDNRB; ETB) | 1.71% |
| guanine nucleotide-binding protein G(I)/G(S)/G(T) beta 1 subunit (GNB1); transducin beta 1 | 1.72% |
| Tyrosine-protein kinase ack | 1.72% |
| BCL2/adenovirus E1B 19-kDa-interacting protein 3 (BNIP3; NIP3) | 1.75% |
| Mitogen-activated protein kinase 10 (MAP kinase 10; MAPK10) | 1.91% |
| Glutamate receptor 1 (GLUR1; GLURA); ionotropic glutamate receptor AMPA 1 (GRIA1) | 2.35% |
| caspase 9 (CASP9) | 2.37% |
| FUSE binding protein | 2.39% |
| Vascular endothelial growth factor C (VEGFC) | 2.41% |
| cyclin-dependent kinase inhibitor 1C (CDKN1C); p57; KIP2 | 2.60% |
| Homeobox protein D3 (HOXD3); HOX4A | 2.66% |
| Neogenin | 2.72% |
| (B) AA from the others | |
| 14-3-3n protein | 1.29% |
| Contactin (CNTN1); glycoprotein gp135 | 1.30% |
| BCL2-like 2 (BCL2L2); BCL-W | 1.32% |
| Mitogen-activated protein kinase kinase 1 (MAP kinase kinase 1; MAPKK1; | 1.34% |
| Ku (p70/p80) subunit; ATP-dependent DNA helicase II | 1.36% |
| Transcription factor HTF4 | 1.37% |
| HER2/Neu | 1.42% |
| PI3 kinase | 1.50% |
| Calgranulin B (CAGB); migration inhibitory factor-related protein 14 (MRP14); leukocyte L1 complex heavy chain; S100 calcium-binding protein A9 (S100A9) | 1.50% |
| Bone morphogenetic protein 2A (BMP2A) | 1.50% |
| Protein kinase C delta (PKC-delta) | 1.51% |
| Mitogen-activated protein kinase 10 (MAP kinase 10; MAPK10) | 1.52% |
| Interleukin 1 receptor type I (IL1R1) | 1.57% |
| Focal adhesion kinase (FADK) | 1.64% |
| Inhibitor of apoptosis protein 2 (hIAP2; IAP2); IAP homolog B; TNFR2-TRAF signaling complex protein 2; MIHC | 1.69% |
| cAMP-dependent protein kinase type I beta regulatory subunit (PRKAR1B) | 1.74% |

AA, anaplastic astrocytoma;
OL, oligodendroglioma.

TABLE 5

Strong Features Found for Glioblastoma Multiforme vs. Other Gliomas

| | Error |
|---|---|
| (A) Common genes | |
| Insulin-like growth factor-binding protein 2 (IGF-binding protein 2; IGFBP2; IBP2) | 4.03% |
| Fibroblast growth factor receptor 1 (FGFR1); basic fibroblast growth factor receptor (BFGFR); fms-like tyrosine kinase 2 (FLT2); heparin-binding growth factor receptor alpha A (HBGFR-alpha A) | 4.05% |
| Pleiotrophin (PTN); osteoblast-specific factor 1 (OSF1); heparin-binding neurite growth-promoting factor 1 (HBNF1; NEGF1); heparin-binding growth-associated molecule (HB-GAM); heparin-binding growth factor 8 (HBGF8) | 4.07% |
| Neural cell adhesion molecule 1 (NCAM1); CD56 antigen; NCAM 140-kDa isoform (NCAM140) + NCAM phosphatidylinositol-linked isoform; NCAM 120-kDa isoform (NCAM120) | 4.24% |
| Cyclin-dependent kinase 4 inhibitor 2D (CDKN2D); p19-INK4D | 4.25% |
| Macrophage inflammatory protein 1 beta (MIP1-beta); T-cell activation protein 2 (AT2); PAT 744; H400; SIS-gamma; lymphocyte activation gene 1 protein (LAG 1); HC21; small inducible cytokine subfamily A member 4 (SCYA4); G 26 T-lymphocyte secreted protein | 4.28% |
| Macrophage inflammatory protein 1 alpha (MIP1-alpha); tonsillar lymphocyte LD78 alpha protein; G0S19-1 protein; PAT 464.2; SIS-beta; small inducible cytokine subfamily A member 3 (SCYA3) | 4.30% |
| Angiopoietin 1 receptor; tyrosine-protein kinase receptor TIE-2; tyrosine-protein kinase receptor TEK; p140 TEK; tunica interna endothelial cell kinase | 4.32% |
| Fms-related tyrosine kinase 1 (FLT1); vascular endothelial growth factor receptor 1 (VEGFR1); vascular permeability factor receptor | 4.38% |
| Endothelial-monocyte activating polypeptide II (EMAP II) | 4.46% |
| Hepatocyte growth factor (HGF); hepatopoietin A (HPTA); scatter factor (SF) | 4.55% |
| Contactin (CNTN1); glycoprotein gp135 | 4.60% |
| Glutamate receptor 1 (GLUR1; GLURA); ionotropic glutamate receptor AMPA 1 (GRIA1) | 4.62% |

TABLE 5-continued

Strong Features Found for Glioblastoma Multiforme vs. Other Gliomas

| | Error |
|---|---|
| (B) AO/GM treated as AO | |
| Natural killer cell enhancing factor (NKEFB); thiol-specific antioxidant protein (TSA); thioredoxin peroxidase 1 (TDPX1); thioredoxin-dependent peroxide reductase 1 | 3.72% |
| Brain-derived neurotrophic factor/neurotrophin 3 receptor (BDNF/NT3 receptor); tyrosine kinase receptor B (TRKB) | 3.75% |
| Cell surface glycoprotein MUC18; melanoma-associated antigen A32; CD146 antigen; melanoma adhesion molecule | 3.91% |
| Bone morphogenetic protein 3 (BMP3); osteogenin | 3.96% |
| Cyclin-dependent kinase inhibitor 1C (CDKN1C); p57; KIP2 | 4.02% |
| Protein-tyrosine phosphatase zeta (R-PTP-zeta) | 4.03% |
| C-1 protein; prefoldin 4 (PFDN4; PFD4) | 4.05% |
| (C) AO/GM treated as GM | |
| Vascular endothelial growth factor C (VEGFC); vascular endothelial growth factor related protein (VRP); FLT4 ligand | 4.19% |
| Cellular retinoic acid-binding protein II (CRABP2) | 4.30% |
| Semaphorin; CD100 antigen | 4.32% |
| Vascular endothelial growth factor (VEGF); vascular permeability factor (VPF) | 4.38% |
| Caspase 9 (CASP9); MCH6; ICE-like apoptotic protease 6 (ICE-LAP6); apoptotic protease activating factor 3 (APAF3) | 4.49% |
| FUSE binding protein | 4.51% |
| Integrin alpha 7B (IGA7B) | 4.59% |
| Endothelin 3 (EDN3; ET3) | 4.62% |

AO, anaplastic oligodendroglioma;
GM, glioblastoma multiforme.

TABLE 6

Strong Features Found for Anaplastic Oligodendroglioma vs. Other Gliomas

| | Error |
|---|---|
| (A) Common genes | |
| Ubiquitin-conjugating enzyme E2 17-kDa (UBE2A); ubiquitin-protein ligase; ubiquitin carrier protein; HR6A | 3.29% |
| cyclin A1 (CCNA1) | 3.32% |
| Interferon gamma (IFN-gamma; IFNG) | 3.35% |
| 6-O-methylguanine-DNA methyltransferase (MGMT); methylated-DNA-protein-cysteine methyltransferase | 3.36% |
| Activator 1 40-kDa subunit (A1 40-kDa subunit); replication factor C 40-kDa subunit (RFC40); RFC2 | 3.38% |
| cyclin G2 (CCNG2) | 3.38% |
| bone morphogenetic protein 4 (BMP4); BMP2B | 3.40% |
| guanine nucleotide-binding protein G-i/G-s/G-t beta subunit 2; transducin beta 2 subunit 2 | 3.42% |
| Urokinase-type plasminogen activator receptor GPI-anchored form (U-PAR; PLAUR); monocyte activation antigen MO3; CD87 antigen | 3.44% |
| (B) AO/GM treated as AO | |
| Acyl-CoA-binding protein (ACBP); diazepam binding inhibitor (DBI); endozepine (EP) | 3.26% |
| Diphtheria toxin receptor (DTR); heparin-binding epidermal growth factor-like growth factor (HBEGF; HEGFL) | 3.31% |
| Homeobox protein 7 (HOX7); MSX1 | 3.34% |
| 45-kDa nuclear factor (NF45) | 3.35% |
| Transcription factor ETR101 | 3.35% |
| cyclin-dependent kinase inhibitor 1A (CDKN1A); melanoma differentiation-associated protein 6 (MDA6); CDK-interacting protein 1 (CIP1); WAF1; SDI1 | 3.39% |
| Endothelin receptor type A (EDNRA; ETA) | 3.40% |
| Oncostatin M (OSM) | 3.40% |
| Transcription initiation factor IID 31-kDa subunit (TFIID); TATA-box-binding protein-associated factor RNA polymerase II G 32-kDa subunit (TAFII32; TAF2G); TAFII31 | 3.41% |
| Placenta growth factor 1 (PLGF1); PLGF2 | 3.43% |
| (C) AO/GM treated as GM | |
| Proto-oncogene tyrosine-protein kinase lck; p56-lck; lymphocyte-specific protein tyrosine kinase (LSK); T-cell-specific protein-tyrosine kinase | 1.42% |
| Inhibitor of DNA binding 1 protein (ID1) | 1.46% |
| WSL protein + TRAMP + Apo-3 + death domain receptor 3 (DDR3) | 1.49% |
| Replication protein A 70-kDa subunit (RPA70; REPA1; RF-A); single-stranded DNA-binding protein | 1.49% |

TABLE 6-continued

Strong Features Found for Anaplastic Oligodendroglioma vs. Other Gliomas

| | Error |
|---|---|
| Interleukin 6 signal transducer (IL6ST); membrane glycoprotein 130 (GP130); oncostatin M receptor | 1.59% |
| Activator 1 37-kDa subunit; replication factor C 37-kDa subunit (RFC37); RFC4 | 1.62% |
| purine-rich element-binding protein A (PURA); purine-rich single-stranded DNA-binding protein alpha (PUR-alpha) | 1.64% |
| cAMP-response element binding protein 1 (CREB1) | 1.67% |
| Prohibitin (PHB) | 1.67% |
| ezrin; cytovillin 2; villin 2 (VIL2) | 1.72% |
| myb proto-oncogene | 1.76% |

AO, anaplastic oligodendroglioma;
GM, glioblastoma multiforme.

Example 3

Discussion

Gliomas are complex cancers whose classification relies upon morphologically based tumor classification schemes that are frequently subjective. Gene expression profiling provides a promising objective approach to method to classify such cancers. Thus, the issue remains as to how to identify the relevant genes that are closely linked to specific disease phenotypes.

The inventors used a novel method to find both strong classifiers and strong features. This method is briefly described in the Materials and Methods section and is explicated in more detail in (Kim et al., 2002). This algorithm considers the inherently variable or "high-noise" nature of microarray measurements and mimics this fuzziness by adding noise to the sample sets. The basic idea is that if the data are deliberately made "worse" and classifier genes can still be identified, then these genes are very likely to be robust.

Using this algorithm, the inventors identified robust classifier gene sets that contain one to three genes that distinguish each type of glioma from the other three. Mostly interestingly, this algorithm resonated with the histologic uncertainties regarding the classification of two cases sharing features of AO and GM that had been assigned to either category based on differing classification criteria. By considering the two cases grouped sequentially first in one category and then the other, the inventors identified different classifier gene sets to distinguish AO from the others and GM from the others. The known functions of the strong feature genes strongly supported the validity of the algorithm, in that, when the vasculature-rich AO/GM cases were placed with other vasculature-rich GMs, the identified strong feature gene set contained several major genes encoding proteins involved in angiogenesis. This suggests that the algorithm is quite robust in identifying genes that are strongly linked to key cellular and tissue phenotypes, and may thus provide a combined molecular-histologic classification scheme that links genotype with phenotype.

Example 4

Prognostic Evaluation of Glioblstoma Multiforme Subjects

MDS analysis (1st component) and hierarchical cluster analysis (1st split) using only the 10 genes listed in Table 7 divides the 15 glioblastoma multiforme patients into two groups: 5 patients with median survival of 36 months, and 10 patients with median survival of 11 months (p=0.0017).

The inventors first computed a number called "the >null Martingale residual" that adjusts the survival time for patients that are still alive. They then computed the rank correlation between this number and each of the 597 genes, and then computed the corresponding t-statistics for these correlation coefficients (by estimating the standard errors and taking the ratios of the coefficients to their standard errors). Fifty-seven genes were significant at the 5% level, but only 10 genes were significant at the 0.5% level. After selecting these 10 genes, the inventors ran Cox proportional hazards regression (again on the ranked expression values) to confirm the significance.

TABLE 7

GBM Prognostic Markers 1. prostaglandin E2 receptor EP4 subtype (PTGER4)
2. ephrin type A receptor 1 (EPHA1)
3. UV excision repair protein RAD23 homolog A (RAD23A; hHR23A)
4. cysteine protease ICE-LAP3
5. growth arrest & DNA damage-inducible protein 153 (GADD153); DNA damage-inducible transcript 3 (DDIT3); C/EBP homologous protein (CHOP)"
6. RNA polymerase II elongation factor SIII p15 subunit
7. sialophorin (SPN); leukosialin (LSN); CD43 antigen
8. OX40 ligand (OX40L); GP34; tax-transcriptionally activated glycoprotein 1 (TXGP1)
9. bone morphogenetic protein 1 (BMP1); procollagen C proteinase 2 (PCP2)
10. interleukin 2 (IL2); T-cell growth factor (TCGF)

The log hazard ratios (standard errors) likelihood ratio p-values for each of the Table 7 genes are provided in Table 8.

TABLE 8

Log Hazard Ratios 1. 0.21 (0.08) 0.0004
2. 0.17 (0.07) 0.0020
3. −0.14 (0.05) 0.0011
4. −0.22 (0.08) 0.0011
5. −0.13 (0.05) 0.0047
6. −0.13 (0.05) 0.0036
7. 0.08 (0.04) 0.016
8. −0.10 (0.04) 0.0054

TABLE 8-continued

Log Hazard Ratios 9.  0.07 (0.03) 0.022
10. −0.10 (0.04) 0.012

Figure 3:
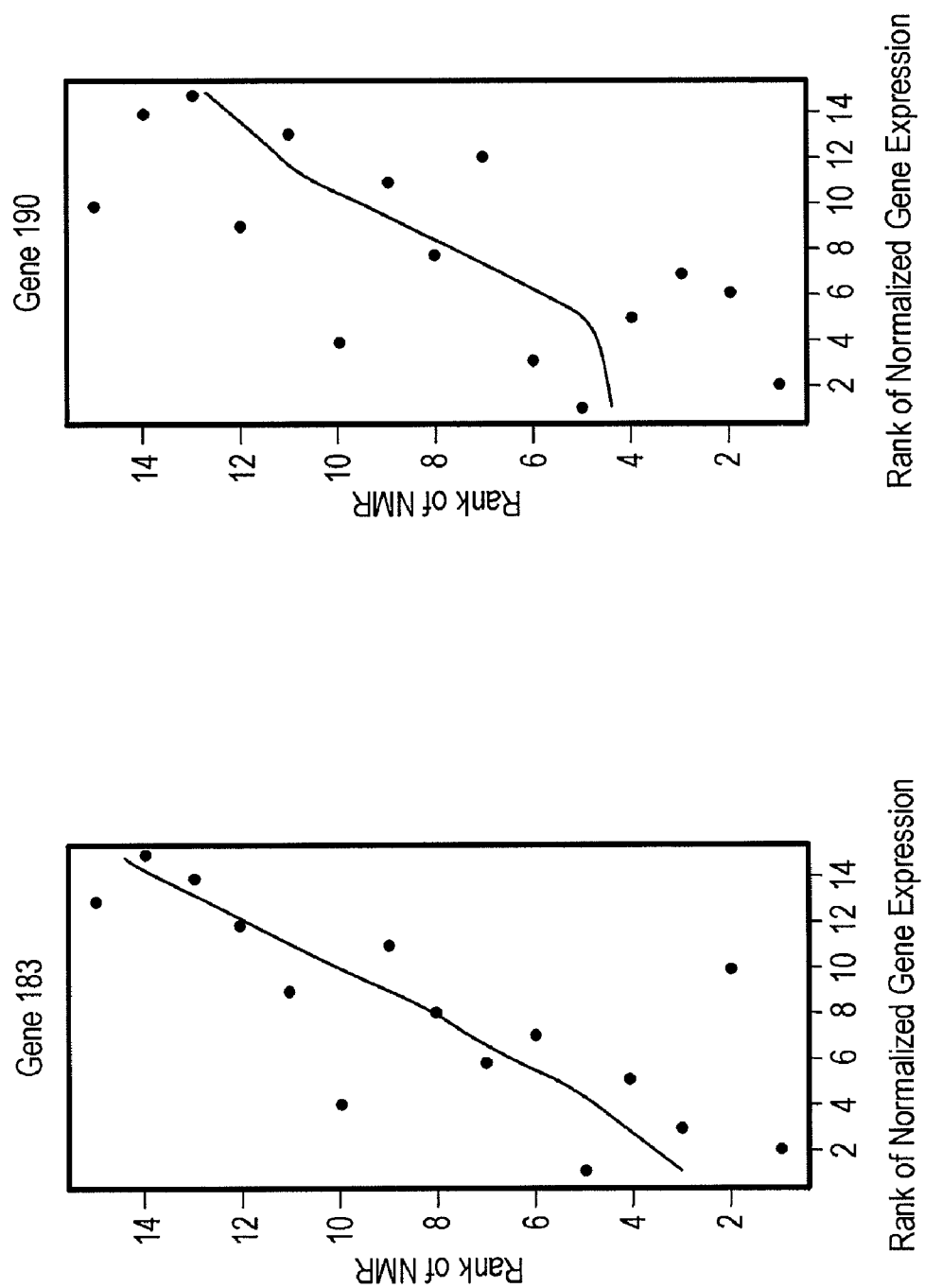
FIG. 3. Graphs showing the 10 glioblastoma multiforme prognostic genes as related to survival. NMR is the survival index, and in the second set of plots deaths is represented by 'x'. The second set of plots is based on smoothing of medians of weighted Kaplan-Meier curves. Gene 183=PTGER4; Gene 190=EPHA1; Gene 231=RAD23A; Gene 236=ICE-LAP3; Gene 245=C/EBP homologous protein; Gene 360=RNA polymerase elongation factor SIII p15 subunit; Gene 453=CD432 antigen; Gene 523=GP34; Gene 562=BMP1; Gene 565=IL2.
Figure 3:
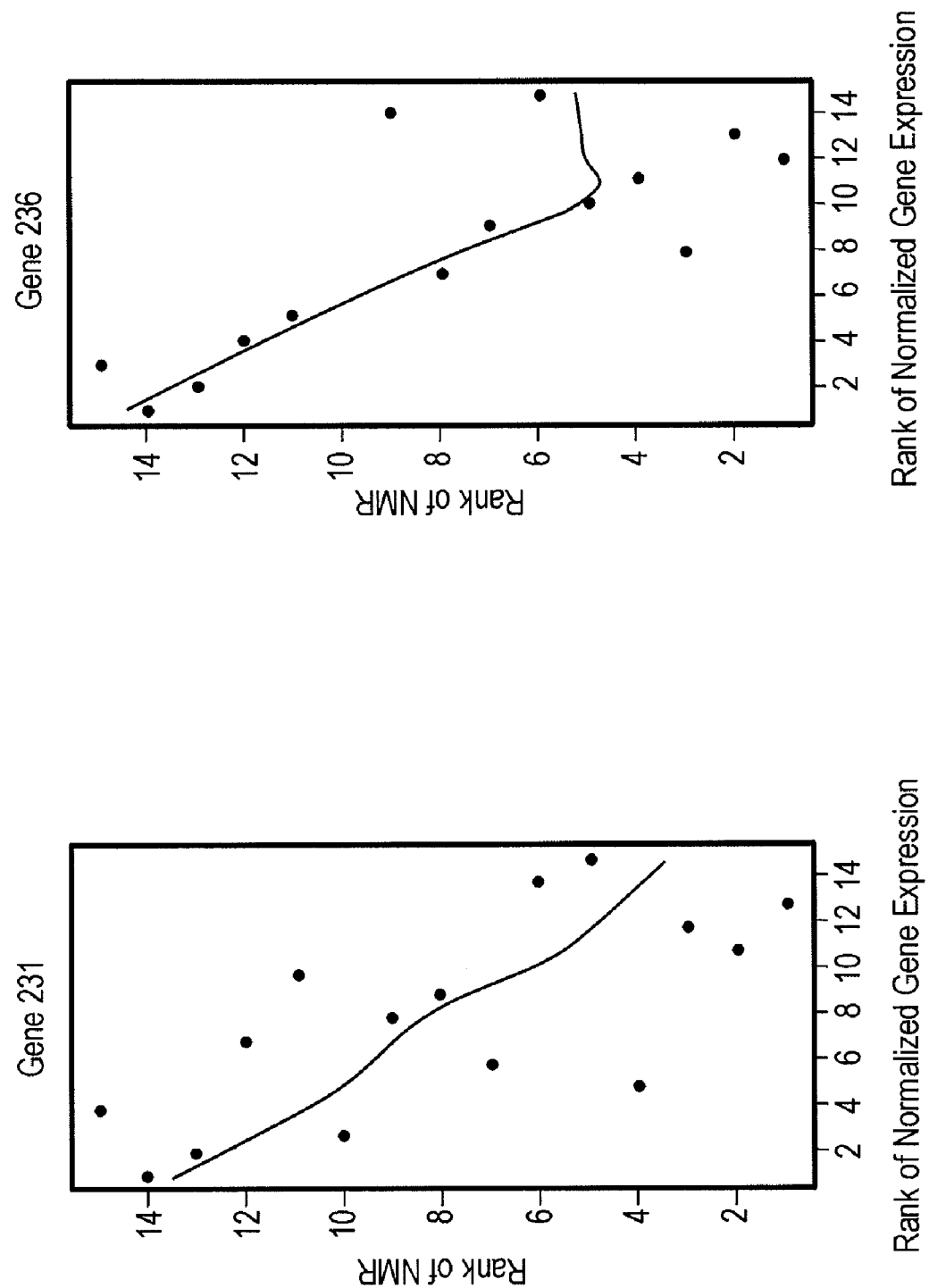
Figure 3:
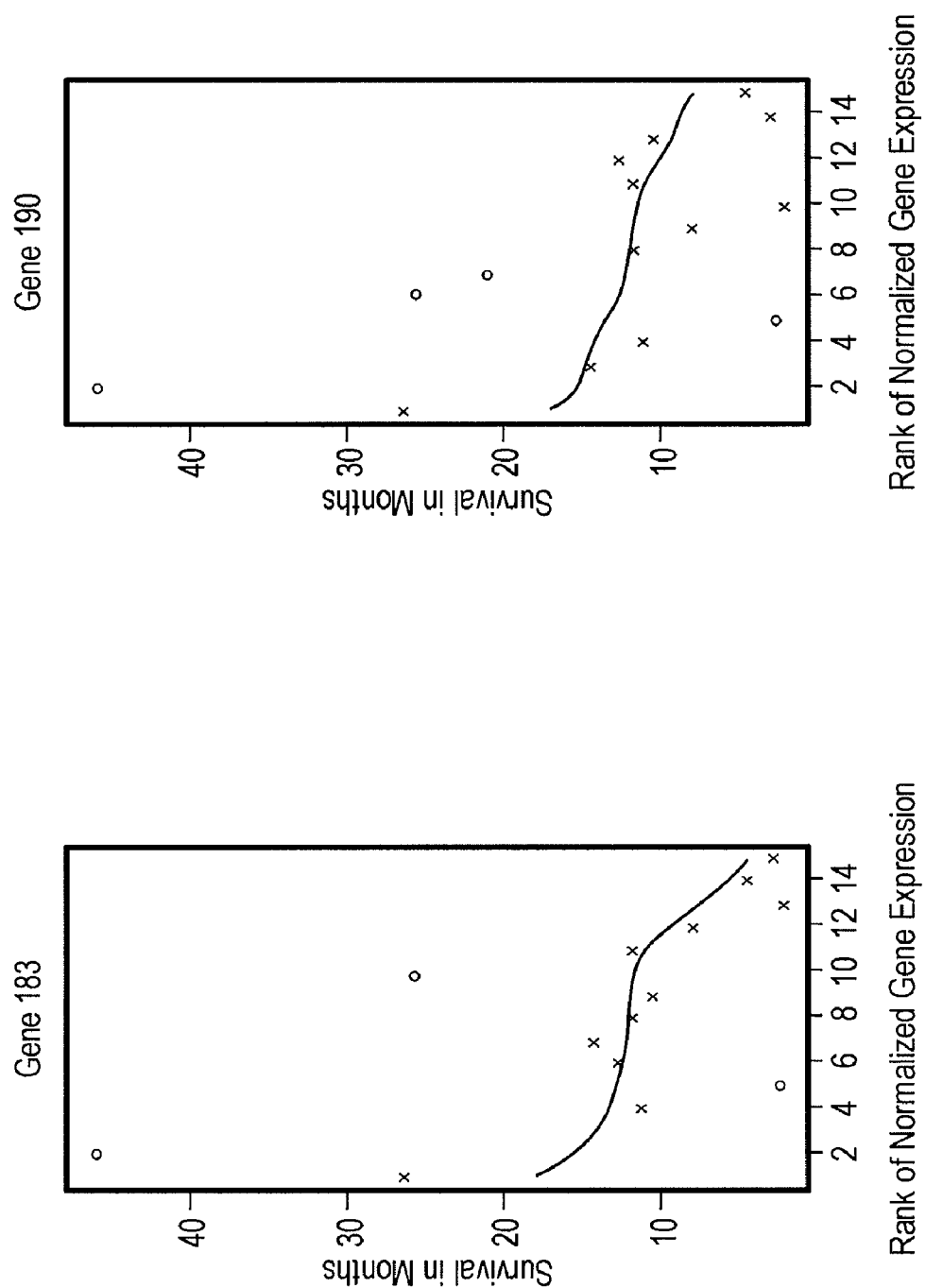
Figure 3:
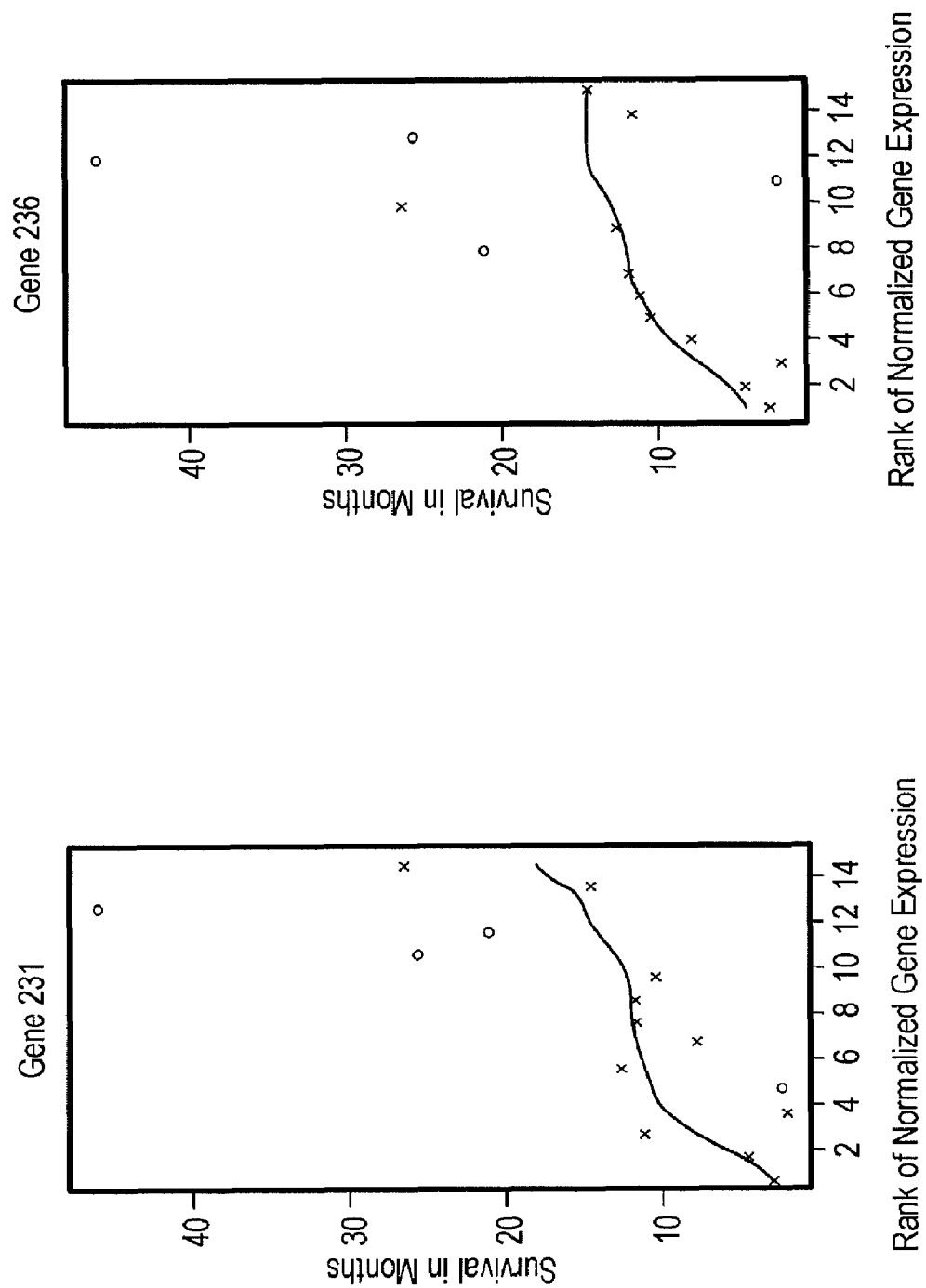
Figure 3:
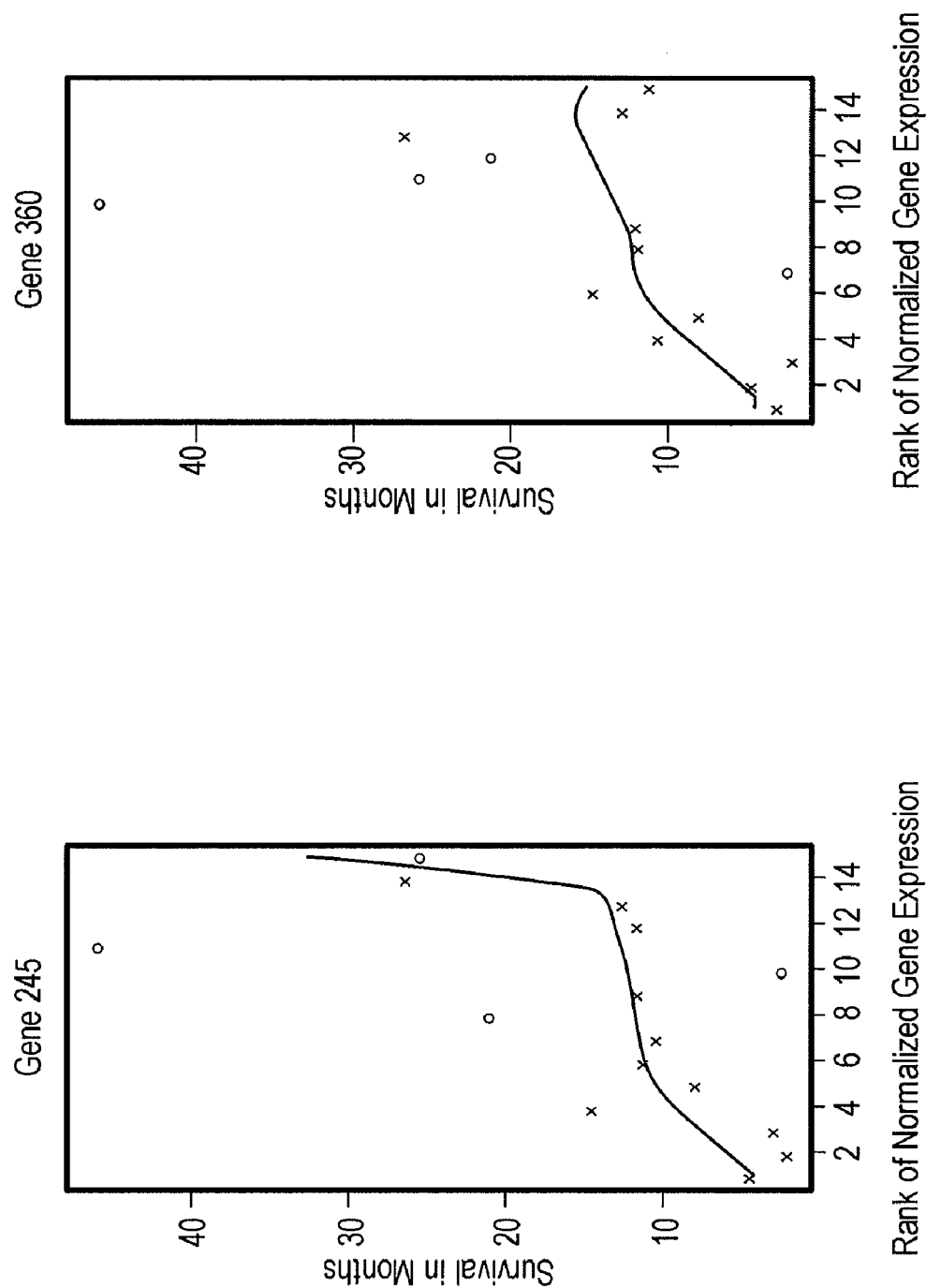
Figure 3:
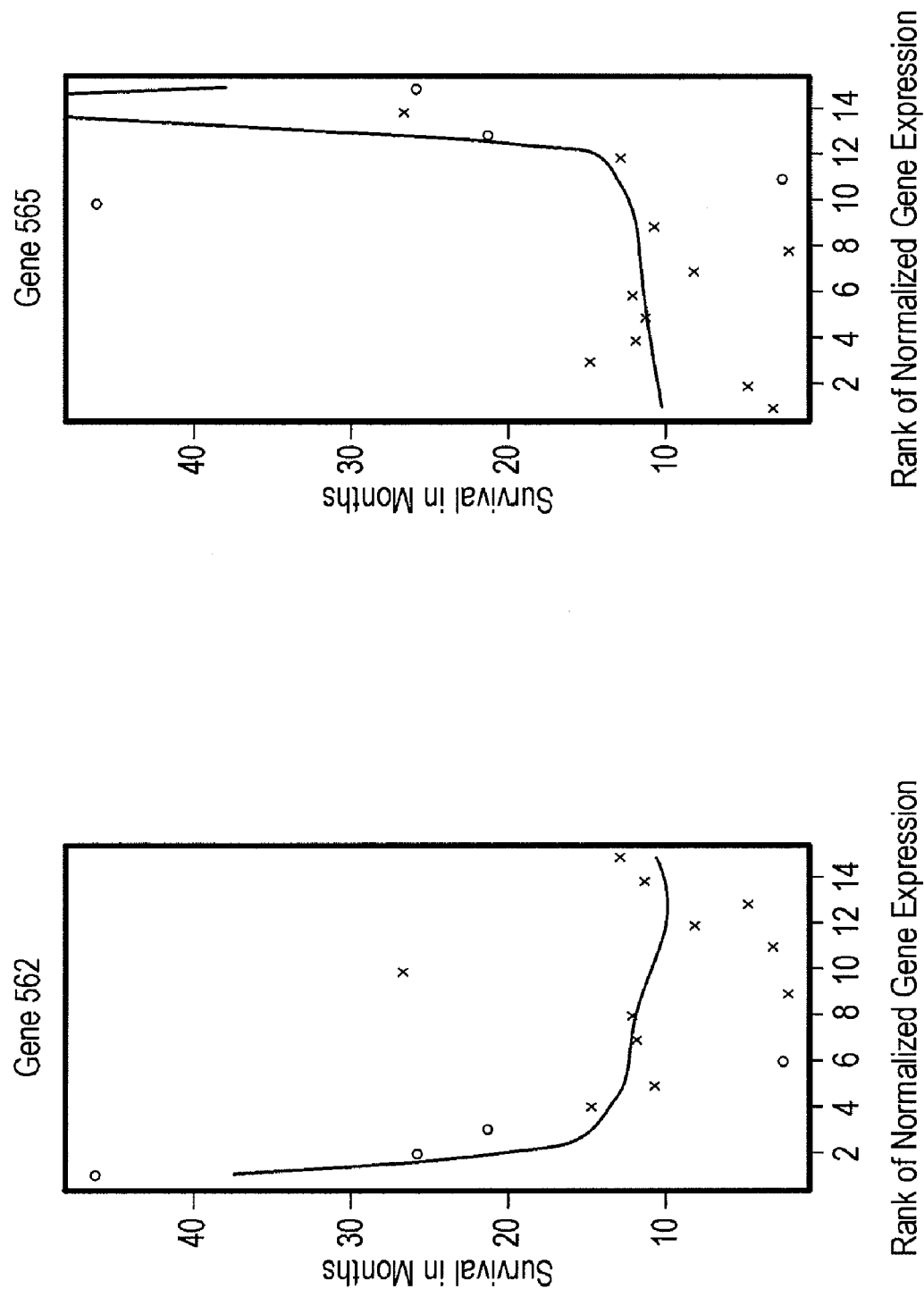
Figure 4A:
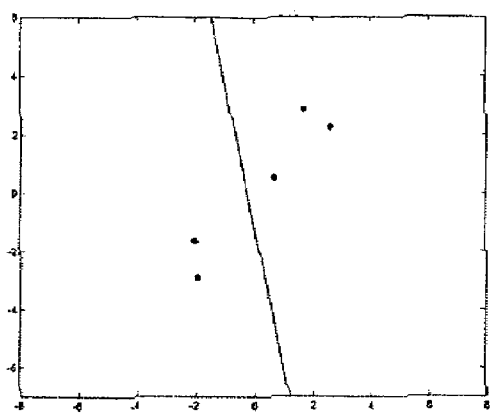
FIGS. 4A-4D. The concept of forming increasingly disperse distributions from the data can be appreciated in this figure, which shows sample points from two classes based on measurements of genes g1 (horizontal axis) and $g^2$ (vertical axis).
Figure 4B:
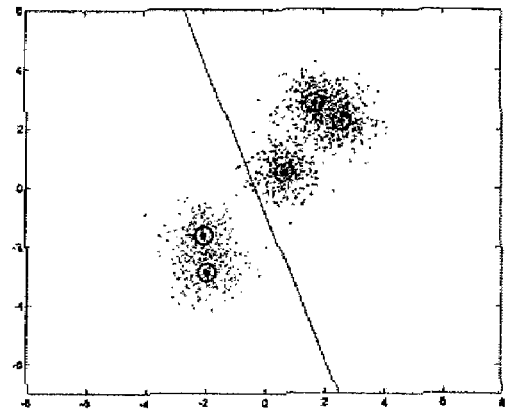
Figure 4C:
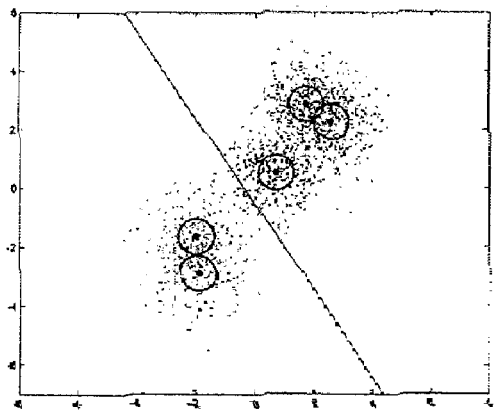
Figure 4D:
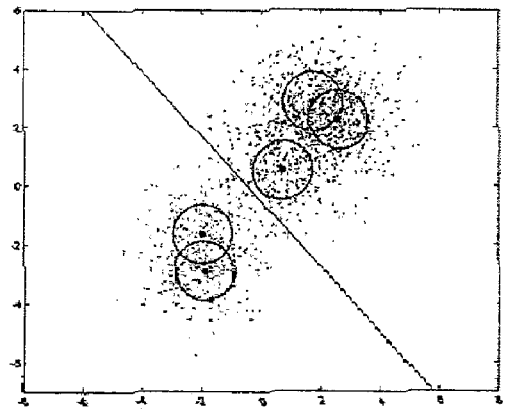
Figure 5A:
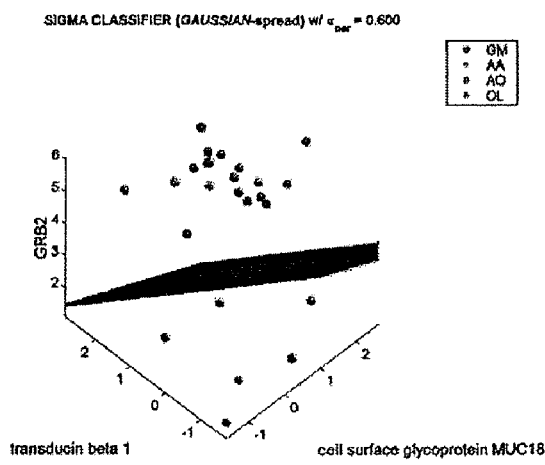
FIGS. 5A-5D. Multivariate discriminators for glioma classifications (examples).
Figure 5B:
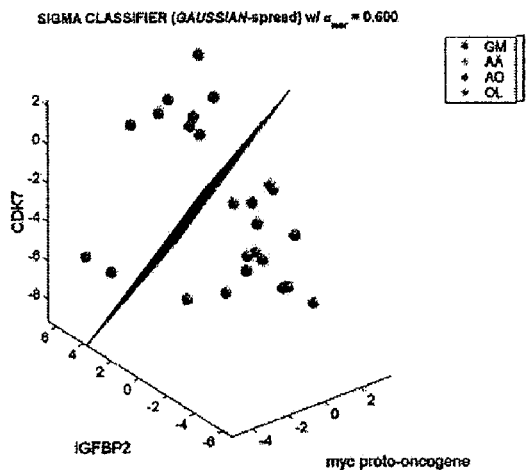
Figure 5C:
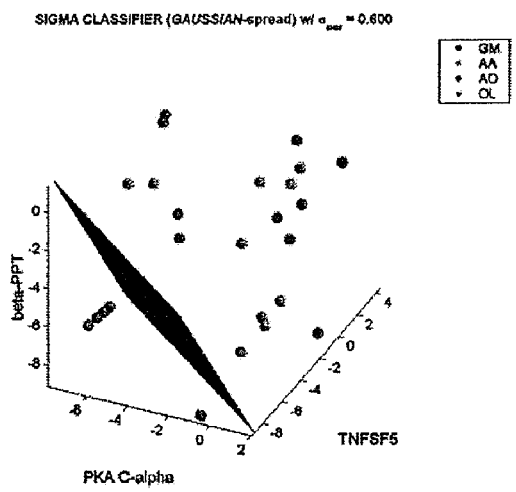
Figure 5D:
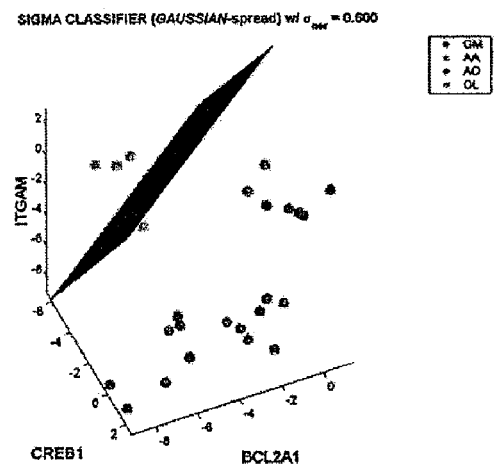

FIG. 3 gives graphs showing how the 10 genes are related to survival. NMR is the magic survival index and in the second set of plots deaths are represented by 'x'. The second set of plots is based on smoothing of medians of weighted Kaplan-Meier curves.

Example 5

Spread Distrubutions

The concept of forming spread distributions from the data is demonstrated in FIG. 4, which shows sample points from two classes based on measurements of genes g1 (horizontal axis) and g2 (vertical axis). FIG. 4A shows a linear classifier derived solely from the sample points. FIGS. 4B-4D, shows samples constructed from the original sample points by deliberately adding artificial random noise of increasing variance to the original points to form larger samples that are spread about the original sample. A linear classifier has been derived for each synthetic sample. Increasing the variance increases the error. A classifier that has a small error for a large variance is desirable because its performance is more likely to be robust relative to new data. Because the implementation of this approach takes a long time if the Monte-Carlo method is used, the actual algorithm used does not use random synthetic data to find the classifier and its error but instead constructs class distributions from the sample data and then finds both the classifier and its error analytically via simple matrix operations (Kim et al., 2002).

Example 6

Classification Analysis for Glioma Data

For any feature set, $\epsilon_\sigma$ denoted the error of the optimal classifier for the feature set, and $\Delta(\epsilon_\sigma)$ denoted the largest decrease in error for the full feature set relative to all of its subsets. The feature sets are first ranked based on the $\sigma$-error, and they are ranked again based on the improvement, $\Delta(\epsilon_\sigma)$. For multiple-gene classifiers, the focus was on feature sets with high rank in both lists. The major focus was to find strong feature sets in which all genes contribute to glioma discrimination.

The algorithm (Kim et al., 2002), which was described briefly in "Materials and Methods," was applied to a set of gene expression profile data derived from 25 human glioma surgical tissue samples. The cDNA microarray experiments were carried out to gain expression information for 597 known cellular genes.

Two-class classifiers were designed for the classification of OL from others, AO from others, AA from others, and GM from others. The number of genes were limited for each classifier to only three, and the dispersion levels (amount of spread) of samples were varied from $\sigma=0.4$ to $\sigma=0.8$. The inventors focused on $\sigma=0.6$ because it provides conservative error estimation, but not too conservative (Kim et al., 2002). Even with analytic classifier design and error estimation, due to the number of potential feature sets and the various cases considered, the computations were done on a Beowulf-based supercomputer (Sterling et al., 1999) at the Center for Information Technology at NIH.

Tables 9-12 show the feature sets identified for each classification category. The tables are constructed so that feature sets ranked high in both $\sigma$-error, $\epsilon_\sigma$, and improvement, $\Delta(\epsilon_\sigma)$, of $\sigma$-error are listed. This is accomplished according to the following scheme: (a) the top three single-gene classifiers for the category are listed in each table; (b) two-gene classifiers ranked in the top $N_2$ pairs for both $\sigma$-error and improvement of $\sigma$-error are included ($N_2$ table-dependent); and (c) three-gene classifiers included in the top $N_3$ triples for both $\epsilon_\sigma$ and $\Delta(\epsilon_\sigma)$ are included ($N_3$ table dependent). For comparison purposes, the LOO error estimate is also shown in the tables. As expected, overall the $\sigma$-error is more conservative, so that when the $\sigma$-error is very small, usually the LOO error is also very small or zero.

To illustrate interpretation of the tables, consider discrimination of OL in Table 9. When selecting multivariate classifiers, all classifiers that include transducin β2 subunit 2 were removed from the list because this gene itself has discriminating power so great that no matter what gene (even a noninformative gene) is used with it, the pairwise T-error is very low (at least as low as for the gene itself). To avoid this kind of redundancy in the tables, there are gene sets omitted from the two- or three-gene lists that possess smaller $\sigma$-errors than those shown in the table. For instance, in Table 9, the $\sigma$-error for the top-listed two-gene set is substantially greater than for any pair involving transducin β2 subunit 2, simply because adjoining genes to transducin β2 subunit 2 produce a $\sigma$-error less than that of transducin β2 subunit 2 itself.

TABLE 9

Feature sets to discriminate OL from others

| Gene names | | | $\epsilon_\sigma$ | $\Delta(\epsilon_\sigma)$ | LOO |
|---|---|---|---|---|---|
| Transducin β2 subunit 2 | | | 0.0207 | | 0.00 |
| Transducin β1 | | | 0.0890 | | 0.08 |
| Growth factor receptor-bound protein 2 | (GRB2) | | 0.1115 | | 0.12 |
| Cyclin D3 | SMARCA4 | | 0.0712 | 0.0986 | 0.04 |
| Follitropin receptor | Thymosin β10 | | 0.0760 | 0.0921 | 0.04 |
| MRP | HSP70.1 | | 0.0761 | 0.0792 | 0.04 |
| MUC18 | Clusterin | TNFSF5 | 0.0804 | 0.0667 | 0.04 |
| MUC18 | Transducin β1 | GRB2 | 0.0156 | 0.0213 | 0.00 |
| MUC18 | Transducin β1 | RXR-β | 0.0310 | 0.0270 | 0.04 |

TABLE 9-continued

Feature sets to discriminate OL from others

| | Gene names | | $\epsilon_\sigma$ | $\Delta(\epsilon_\sigma)$ | LOO |
|---|---|---|---|---|---|
| MUC18 | Transducin β1 | Clusterin | 0.0319 | 0.0260 | 0.00 |
| MUC18 | BCL-W | GRB2 | 0.0364 | 0.0303 | 0.04 |
| MUC18 | Transducin α1 | α1 catenin | 0.0364 | 0.0215 | 0.04 |
| MAP kinase 10 | SMARCA4 | Neuronal acetylcholine Receptor α3 | 0.0397 | 0.0531 | 0.00 |
| MUC18 | GRB2 | Erythropoietin receptor | 0.0406 | 0.0256 | 0.04 |
| Clusterin | ISGF3γ | Erythropoietin receptor | 0.0431 | 0.0462 | 0.00 |

Multivariate discriminatory power is clearly demonstrated in Table 9 with regard to cell surface glycoprotein MUC18. The gene does not appear on the single-gene list, indicating that its σ-error exceeds 0.1115; however, it appears with clusterin (CLU) in the two-gene list and both with and without clusterin (CLU) in the three-gene list. The substantial improvement in each case demonstrates the significant contributions of the genes within each gene set.

There are other instances where the improvement of classification error is sufficient to warrant inclusion in a table. In Table 10, even though IGFBP2 is by itself a decent discriminator, when it is combined with others, such as ephrin type A receptor 1 (EPHA1), the error is significantly improved. The σ-error decreases by more than 0.05, from 0.1392 (data not shown) to 0.0862. The improvement for the LOO error is more significant, from 0.16 (4 of 25) to 0 (0 of 25). Because of this, feature sets including IGFBP2 are shown in the table. The inventors recently studied IGFBP2 expression in 256 cases of gliomas of different grades using tissue microarray and found that IGFBP2 is overexpressed in 80% of GBMs (Wang et al., 2002). Some of these multivariate discriminators are shown in FIG. 5.

In Table 9, only pairwise classifiers that ranked at higher than $100^{th}$ in both lists are included. Triplet-wise classifiers are included only when they are ranked at higher than $50^{th}$ in both lists. For any feature set, $\epsilon_\sigma$ denotes the error of the optimal classifier for the feature set, and $\Delta(\epsilon_\sigma)$ denotes the largest decrease in error for the full feature set relative to all of its subsets. LOO is computed by designing n classifiers from sample subsets formed by leaving out one data point at a time, and then each classifier is applied to the left-out point, and the estimator LOO is 1/n times the number of errors by the n classifiers.

TABLE 10

Feature sets to discriminate GM from others
Pairwise classifiers are selected when they are ranked at higher than $200^{th}$ in both lists, and triplet-wise classifiers are selected only when ranked at higher than $50^{th}$.

| Gene names | | | $\epsilon_\sigma$ | $\Delta(\epsilon_\sigma)$ | LOO |
|---|---|---|---|---|---|
| TIE-2 | | | 0.1315 | | 0.12 |
| IGFBP2 | | | 0.1392 | | 0.16 |
| VEGFR1 | | | 0.2113 | | 0.16 |
| TIE-2 | TNFSF5 | | 0.0796 | 0.0519 | 0.08 |
| IGFBP2 | EPHA1 | | 0.0861 | 0.0531 | 0.00 |
| IGFBP2 | CDK7 | | 0.0879 | 0.0513 | 0.08 |
| IGFBP2 | TNFSF5 | | 0.0911 | 0.0481 | 0.04 |
| myc | IGFBP2 | CDK7 | 0.0582 | 0.0297 | 0.00 |
| IGFBP2 | TNFSF5 | CC chemokine receptor type 2 | 0.0591 | 0.0320 | 0.00 |
| TIE-2 | CXC chemokine receptor type 4 | EPHA1 | 0.0623 | 0.0322 | 0.04 |
| TIE-2 | CDK7 | JAK3 | 0.0634 | 0.0302 | 0.04 |
| TIE-2 | IGFBP2 | JAK3 | 0.0660 | 0.0315 | 0.08 |

TABLE 11

Feature sets to discriminate AO from others
Pairwise classifiers are selected when they are ranked at higher than $10^{th}$ in both lists, and triplet-wise classifiers are selected only when ranked at highe than $50^{th}$.

| Gene names | | | $\epsilon_\sigma$ | $\Delta(\epsilon_\sigma)$ | LOO |
|---|---|---|---|---|---|
| DNase | | | 0.1556 | | 0.28 |
| TNFSF5 | | | 0.1658 | | 0.20 |
| RAD50 | | | 0.1659 | | 0.20 |
| TNFSF5 | DNase X | | 0.0750 | 0.0806 | 0.04 |
| Prostaglandin E2 receptor EP4 | DNase X | | 0.0784 | 0.0772 | 0.08 |
| GNA13 | TNFSF5 | | 0.0826 | 0.0832 | 0.08 |

TABLE 11-continued

Feature sets to discriminate AO from others
Pairwise classifiers are selected when they are ranked at higher than 10th in both lists, and triplet-wise classifiers are selected only when ranked at highe than 50th.

| Gene names | | | $\epsilon_\sigma$ | $\Delta(\epsilon_\sigma)$ | LOO |
|---|---|---|---|---|---|
| Prostaglandin E2 receptor EP4 | TNFRSF5 | | 0.0907 | 0.0947 | 0.08 |
| RAB5A | TNFSF5 | | 0.0909 | 0.0749 | 0.16 |
| erbB4 | Prostaglandin E2 receptor EP4 | | 0.1012 | 0.0841 | 0.08 |
| PKA C-α | TNFSF5 | Preprotachykinin β | 0.0529 | 0.0549 | 0.04 |
| DNase X | RκB DNA-binding protein | Preprotachykinin β | 0.0534 | 0.0479 | 0.04 |
| PKA C-α | DNA ligase IV | TNFSF5 | 0.0591 | 0.0488 | 0.04 |
| DNA ligase IV | TNFSF5 | Acidic fibroblast growth factor | 0.0616 | 0.0474 | 0.04 |

TABLE 12

Feature sets to discriminate AA from others
Pairwise classifiers are selected when they are ranked at higher than 100th in both lists, and triplet-wise classifiers are selected only when ranked at higher than 50th

| Gene names | | | $\epsilon_\sigma$ | $\Delta(\epsilon_\sigma)$ | LOO |
|---|---|---|---|---|---|
| CREB1 | | | 0.1018 | | 0.20 |
| IFN-_receptor 2 | | | 0.1208 | | 0.12 |
| DCC | | | 0.1210 | | 0.16 |
| CREB1 | RAB3A | | 0.0695 | 0.0323 | 0.16 |
| CREB1 | IL2R-γ | | 0.0745 | 0.0273 | 0.12 |
| Cyclin E | CREB1 | | 0.0759 | 0.0258 | 0.12 |
| CREB1 | MAP kinase 10 | | 0.0761 | 0.0257 | 0.12 |
| CREB1 | BCL2A1 | | 0.0761 | 0.0256 | 0.08 |
| U-PAR | VEGFR2 | | 0.0855 | 0.0704 | 0.12 |
| U-PAR | FADK | | 0.0917 | 0.0641 | 0.17 |
| U-PAR | HTF4 | | 0.0935 | 0.0597 | 0.16 |
| CREB1 | BCL2A1 | CD11B | 0.0511 | 0.0250 | 0.04 |
| CREB1 | VEGFR2 | Thymosin β10 | 0.0565 | 0.0231 | 0.04 |
| CREB1 | VEGFR2 | CD11B antigen | 0.0584 | 0.0212 | 0.08 |
| Cyclin E | CREB1 | Thymosin β10 | 0.0587 | 0.0173 | 0.08 |
| CREB1 | BCL2A1 | Endothelin receptor type A | 0.0588 | 0.0174 | 0.04 |
| U-PAR | CREB1 | VEGFR2 | 0.0592 | 0.0204 | 0.08 |
| p55-FGR | Cyclin E | CREB1 | 0.0592 | 0.0167 | 0.08 |
| CREB1 | BCL2A1 | IL12-α | 0.0599 | 0.0162 | 0.04 |
| CREB1 | VEGFR2 | Caspase 2 | 0.0607 | 0.0189 | 0.08 |
| CREB1 | VEGFR2 | SCYB5 | 0.0623 | 0.0173 | 0.08 |

Example 7

Clustering

To aid in understanding the gene expression characteristics of the selected feature sets, all of the genes in the data set are clustered in such a way as to be close to other genes with similar expression. This is accomplished via hierarchical clustering using the Pearson correlation and average linkage. An added value to the clustering is that genes with known behavior can be used to analyze the results, and genes with unknown behavior can be placed into certain pathways for future functional testing.

A global clustering map was developed for the hierarchical clustering analysis. Four clusters are interesting with regard to discriminating OL and GM. Most genes found to singly discriminate OL from other types of glioma appear in the first cluster extracted, and they are underexpressed in OL. Most genes found to classify GM from other types lie in the other three extracted clusters. In the first cluster, most of the genes are overexpressed in GM and underexpressed in AO and OL; in the second cluster, they are overexpressed in GM and underexpressed in OL; and in the third cluster, they are slightly underexpressed in GM.

Most genes identified as singly but only marginally classifying AO from the others are not clustered together as well as in the OL and the GM cases, nor are those classifying AA from the others. This is interesting because it is consistent with the fact AO and AA represent more heterogeneous characteristics of the cancer. This supports the usefulness of the multivariate approach.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

IX. REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,683,195
U.S. Pat. No. 4,683,202
U.S. Pat. No. 4,684,611
U.S. Pat. No. 4,797,368
U.S. Pat. No. 4,800,159
U.S. Pat. No. 4,883,750
U.S. Pat. No. 4,952,500
U.S. Pat. No. 5,139,941
U.S. Pat. No. 5,242,974
U.S. Pat. No. 5,279,721
U.S. Pat. No. 5,302,523
U.S. Pat. No. 5,322,783
U.S. Pat. No. 5,384,253
U.S. Pat. No. 5,384,261
U.S. Pat. No. 5,405,783
U.S. Pat. No. 5,412,087
U.S. Pat. No. 5,424,186
U.S. Pat. No. 5,429,807
U.S. Pat. No. 5,436,327
U.S. Pat. No. 5,445,934
U.S. Pat. No. 5,464,765
U.S. Pat. No. 5,472,672
U.S. Pat. No. 5,527,681
U.S. Pat. No. 5,529,756
U.S. Pat. No. 5,532,128
U.S. Pat. No. 5,538,877
U.S. Pat. No. 5,538,880
U.S. Pat. No. 5,545,531
U.S. Pat. No. 5,550,318
U.S. Pat. No. 5,554,501
U.S. Pat. No. 5,556,752
U.S. Pat. No. 5,561,071
U.S. Pat. No. 5,563,055
U.S. Pat. No. 5,571,639
U.S. Pat. No. 5,580,859
U.S. Pat. No. 5,589,466
U.S. Pat. No. 5,591,616
U.S. Pat. No. 5,593,839
U.S. Pat. No. 5,599,695
U.S. Pat. No. 5,610,042
U.S. Pat. No. 5,624,711
U.S. Pat. No. 5,656,610
U.S. Pat. No. 5,658,734
U.S. Pat. No. 5,700,637
U.S. Pat. No. 5,702,932
U.S. Pat. No. 5,736,524
U.S. Pat. No. 5,780,448
U.S. Pat. No. 5,789,215
U.S. Pat. No. 5,840,873
U.S. Pat. No. 5,843,640
U.S. Pat. No. 5,843,650
U.S. Pat. No. 5,843,651
U.S. Pat. No. 5,843,663
U.S. Pat. No. 5,846,708
U.S. Pat. No. 5,846,709
U.S. Pat. No. 5,846,717
U.S. Pat. No. 5,846,726
U.S. Pat. No. 5,846,729
U.S. Pat. No. 5,846,783
U.S. Pat. No. 5,849,481
U.S. Pat. No. 5,849,486
U.S. Pat. No. 5,849,487
U.S. Pat. No. 5,849,497
U.S. Pat. No. 5,849,546
U.S. Pat. No. 5,849,547
U.S. Pat. No. 5,851,772
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,244
U.S. Pat. No. 5,863,732
U.S. Pat. No. 5,863,753
U.S. Pat. No. 5,866,331
U.S. Pat. No. 5,866,336
U.S. Pat. No. 5,882,864
U.S. Pat. No. 5,900,481
U.S. Pat. No. 5,905,024
U.S. Pat. No. 5,910,407
U.S. Pat. No. 5,912,124
U.S. Pat. No. 5,912,145
U.S. Pat. No. 5,912,148
U.S. Pat. No. 5,916,776
U.S. Pat. No. 5,916,779
U.S. Pat. No. 5,919,626
U.S. Pat. No. 5,919,630
U.S. Pat. No. 5,922,574
U.S. Pat. No. 5,925,517
U.S. Pat. No. 5,925,565
U.S. Pat. No. 5,928,862
U.S. Pat. No. 5,928,869
U.S. Pat. No. 5,928,905
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,819
U.S. Pat. No. 5,935,825
U.S. Pat. No. 5,939,291
U.S. Pat. No. 5,942,391
U.S. Pat. No. 5,945,100
U.S. Pat. No. 5,981,274
U.S. Pat. No. 5,994,136
U.S. Pat. No. 5,994,624
U.S. Pat. No. 6,004,755
U.S. Pat. No. 6,013,516
Abbondanzo, *Ann Diagn Pathol,* 3(5):318-327, 1999.
Alizadeh et al., *Nature* 403 (6769), 503-511, 2000.
Allred et al., *Arch Surg,* 125(1):107-13, 1990.
Almendro et al., *J Immunol.,* 157:5411-5421, 1996.
Angel et al., *Mol. Cell. Biol.,* 7:2256, 1987.
Angel et al., *Cell,* 49:729, 1987b.
Angel et al., *Mol. Cell. Biol.,* 7:2256, 1987a.

Antibodies: A Laboratory Manual, Cold Spring Harbor Laboratory, Cold Spring Harbor Press, Cold Spring Harbor, N.Y., 1988.
Atchison and Perry, *Cell,* 46:253, 1986.
Atchison and Perry, *Cell,* 48:121, 1987.
Ausubel et al., In: *Current Protocols in Molecular Biology,* John, Wiley & Sons, Inc, New York, 1994.
Baichwal and Sugden, In: *Gene Transfer,* Kucherlapati (ed.), New York, Plenum Press, 117-148, 1986.
Banerji et al., *Cell,* 27(2 Pt 1):299-308, 1981.
Banerji et al., *Cell,* 33(3):729-740, 1983.
Ben-Dor et al., *J Comput. Biol.* 7(3-4): 559-583, 2000.
Berkhout et al., *Cell,* 59:273-282, 1989.
Bittner et al., *Nature* 406 (6795), 536-40, 2000.
Blanar et al., *EMBO J,* 8:1139, 1989.
Blomer et al., *J Virol.,* 71(9):6641-6649, 1997.
Bodine and Ley, *EMBO J.,* 6:2997, 1987.
Borg and Groenen, In: *Modern multidimensional scaling: Theory and applications.* Springer, New York. 1997
Boshart et al., *Cell,* 41:521, 1985.
Bosze et al., *EMBO J,* 5(7):1615-1623, 1986.
Braddock et al., *Cell,* 58:269, 1989.
Brown et al., *Immunol Ser,* 53:69-82, 1990.
Bulla and Siddiqui, *J. Virol.,* 62:1437, 1986.
Campbell and Villarreal, *Mol. Cell. Biol.,* 8:1993, 1988.
Campere and Tilghman, *Genes and Dev.,* 3:537, 1989.
Campo et al., *Nature,* 303:77, 1983.
Carbonelli et al., *FEMS Microbiol Lett,* 177(1):75-82, 1999.
Celander and Haseltine, *J. Virology,* 61:269, 1987.
Celander et al., *J Virology,* 62:1314, 1988.
Chamberlan et al., In: *PCR Protocols,* eds. Innis, Gelfand, Sninsky, White (Academic Press, NY, 272-281, 1990.
Chandler et al., *Cell,* 33:489, 1983.
Chandler et al., *Proc Natl Acad Sci USA,* 94(8):3596-601, 1997.
Chang et al., *Mol. Cell. Biol.,* 9:2153, 1989.
Chatterjee et al., *Proc Natl. Acad Sci. U.S.A.,* 86:9114, 1989.
Chen and Okayama, *Mol. Cell Biol.,* 7(8):2745-2752, 1987.
Choi et al., *Cell,* 53:519, 1988.
Cocea, *Biotechniques,* 23(5):814-816, 1997.
Cohen et al., *J. Cell. Physiol.,* 5:75, 1987.
Costa et al., *Mol. Cell. Biol.,* 8:81, 1988.
Cotten et al., *Proc Natl Acad Sci USA,* 89(13):6094-6098, 1992.
Coupar et al., *Gene,* 68:1-10, 1988.
Cripe et al., *EMBO J.,* 6:3745, 1987.
Culotta and Hamer, *Mol. Cell. Biol.,* 9:1376, 1989.
Curiel, *Nat Immun,* 13(2-3):141-64, 1994.
Dandolo et al., *J. Virology,* 47:55-64, 1983.
Daumas-Duport et al., *Cancer* 62, 2152-2165, 1988.
De Jager et al., *Semin Nucl Med* 23(2):165-179, 1993.
De Villiers et al., *Nature,* 312(5991):242-246, 1984.
Deschamps et al., *Science,* 230:1174-1177, 1985.
Devroye et al., *Theory of Pattern Recognition,* NY, Springer (Ed.), 1996.
Doolittle et al., *Methods Mol Biol.,* 109:215-237, 1999.
Dougherty, *Comparative and Functional Genomics* 2:28-34, 2001.
Edbrooke et al., *Mol. Cell. Biol.,* 9:1908, 1989.
Edlund et al., *Science,* 230:912-916, 1985.
European Application No. 0 364 255
European Application No. 320 308
European Application No. EPO 0273085
European Application No. GB 2 202 328
European Application No.329 822
Fechheimer et al., *Proc. Nat'l Acad. Sci. USA,* 84:8463-8467, 1987.
Feng and Holland, *Nature,* 334:6178, 1988.
Firak and Subramanian, *Mol. Cell. Biol.,* 6:3667, 1986.
Foecking and Hofstetter, *Gene,* 45(1):101-105, 1986.
Fraley et al., *Proc. Nat'l Acad. Sci. USA,* 76:3348-3352, 1979.
Friedmann, *Science,* 244:1275-1281, 1989.
Frohman, In: *PCR Protocols: A Guide To Methods And Applications,* Academic Press, N.Y., 1990.
Fujita et al., *Cell,* 49:357, 1987.
Fuller et al., *Cancer Res.* 59, 4228-4232, 1999.
Ghosh and Bachhawat, In: *Liver Diseases, Targeted Diagnosis and Therapy Using Specific Receptors and Ligands.* Wu et al., eds., Marcel Dekker, New York, pp. 87-104, 1991.
Gilles et al., *Cell,* 33:717, 1983.
Gloss et al., *EMBO J.,* 6:3735, 1987.
Godbout et al., *Mol. Cell. Biol.,* 8:1169, 1988.
Golub et al., *Science* 286, 531-537, 1999.
Goodbourn and Maniatis, *Proc. Nat'l Acad. Sci. USA,* 85:1447, 1988.
Goodbourn et al., *Cell,* 45:601, 1986.
Gopal, *Mol. Cell Biol.,* 5:1188-1190, 1985.
Graham and Van Der Eb, *Virology,* 52:456-467, 1973.
Greene et al., *Immunology Today,* 10:272, 1989
Grosschedl and Baltimore, *Cell,* 41:885, 1985.
Grunhaus et al., *Seminar in Virology,* 200(2):535-546, 1992.
Gulbis and Galand, *Hum Pathol* 24(12):1271-1285, 1993.
Harland and Weintraub, *J. Cell Biol.,* 101:1094-1099, 1985.
Haslinger and Karin, *Proc. Nat'l Acad. Sci. USA,* 82:8572, 1985.
Hauber and Cullen, *J. Virology,* 62:673, 1988.
Hedenfalk et al., *N Engl J Med* 244, 539-548, 2001.
Hen et al., *Nature,* 321:249, 1986.
Hensel et al., *Lymphokine Res.,* 8:347, 1989.
Herr and Clarke, *Cell,* 45:461, 1986.
Hirochika et al., *J. Virol.,* 61:2599, 1987.
Hirsch et al., *Mol. Cell. Biol.,* 10:1959, 1990.
Holbrook et al., *Virology,* 157:211, 1987.
Horlick and Benfield, *Mol. Cell. Biol.,* 9:2396, 1989.
Horwich et al., *Virol.,* 64:642-650, 1990.
Huang et al., *Cell,* 27:245, 1981.
Hug et al., *Mol. Cell. Biol.,* 8:3065, 1988.
Hwang et al., *Mol. Cell. Biol.,* 10:585, 1990.
Irnagawa et al., *Cell,* 51:251, 1987.
Imbra and Karin, *Nature,* 323:555, 1986.
Imler et al., *Mol. Cell. Biol,* 7:2558, 1987.
Imperiale and Nevins, *Mol. Cell. Biol.,* 4:875, 1984.
Inouye and Inouye, *Nucleic Acids Res.,* 13: 3101-3109, 1985.
Jakobovits et al., *Mol. Cell. Biol.,* 8:2555, 1988.
Jameel and Siddiqui, *Mol. Cell. Biol.,* 6:710, 1986.
Jaynes et al., *Mol. Cell. Biol.,* 8:62, 1988.
Johnson et al., *Mol. Cell. Biol.,* 9:3393, 1989.
Kadesch and Berg, *Mol. Cell. Biol.,* 6:2593, 1986.
Kaeppler et al., *Plant Cell Reports* 9: 415-418, 1990.
Kaneda et al., *Science,* 243:375-378, 1989.
Karin et al., *Mol. Cell. Biol.,* 7:606, 1987.
Katinka et al., *Cell,* 20:393, 1980.
Kato et al., *J Biol. Chem.,* 266:3361-3364, 1991.
Kawamoto et al., *Mol. Cell. Biol.,* 8:267, 1988.
Kelleher and Vos, *Biotechniques,* 17(6):1110-7, 1994.
Kendall and Gibbons, *Rank Correlation Methods,* Fifth Edition. Oxford University Press, New York. 1990.
Khan et al., *Nature Medicine* 7(6): 673-679, 2001.
Kiledjian et al., *Mol. Cell. Biol.,* 8:145, 1988.
Kim et al., *J. Comput. Biol.* 9:129-148, 2002.
Klamut et al., *Mol. Cell. Biol.,* 10:193, 1990.

Kleihues and Cavenee, World Health Organzation Classification of Tumours of the Nervous System, New York: Oxford University Press, 2000.
Klein et al., *Nature*, 327:70-73, 1987.
Koch et al., *Mol. Cell. Biol.*, 9:303, 1989.
Kraus et al. *FEBS Lett.*, 428(3):165-170, 1998.
Kriegler and Botchan, In: *Eukaryotic Viral Vectors*, Y. Gluzman, ed., Cold Spring Harbor: Cold Spring Harbor Laboratory, NY, 1982.
Kriegler and Botchan, *Mol. Cell. Biol*, 3:325, 1983.
Kriegler et al., *Cell*, 38:483, 1984.
Kriegler et al., *Cell*, 53:45, 1988.
Kuhl et al., *Cell*, 50:1057, 1987.
Kunz et al., *Nucl. Acids Res.*, 17:1121, 1989.
Kwoh et al., *Proc. Nat. Acad. Sci. USA*, 86: 1173, 1989.
Lareyre et al., *J Biol Chem.*, 274(12):8282-8290, 1999.
Larsen et al., *Proc Natl. Acad. Sci. USA.*, 83:8283, 1986.
Laspia et al., *Cell*, 59:283, 1989.
Latimer et al., *Mol. Cell. Biol.*, 10:760, 1990.
Laughlin et al., *J. Virol.*, 60(2):515-524, 1986.
Lebkowski et al., *Mol. Cell. Biol.*, 8(10):3988-3996, 1988.
Lee et al., *J Auton Nerv Syst.* 74(2-3):86-90, 1997.
Lee et al., *Nature*, 294:228, 1981.
Lee et al., *Nucleic Acids Res.*, 12:4191-206, 1984.
Levenson et al., *Hum Gene Ther*, 9(8):1233-6, 1998.
Levinson et al., *Nature*, 295:79, 1982.
Lin et al., *Mol. Cell. Biol.*, 10:850, 1990.
Luria et al., *EMBO J.*, 6:3307, 1987.
Lusky and Botchan, *Proc Natl. Acad. Sci. U.S.A.*, 83:3609, 1986.
Lusky et al., *Mol. Cell. Biol.* 3:1108, 1983.
Macejak and Samow, *Nature*, 353:90-94, 1991.
Majors and Varmus, *Proc. Nat'l Acad. Sci. USA*, 80:5866, 1983.
Maniatis, et al., Molecular Cloning, A Laboratory Manual, Cold Spring Harbor Press, Cold Spring Harbor, N.Y., 1989.
Mann et al., *Cell*, 33:153-159, 1983.
McLaughlin et al., *J. Virol.*, 62(6):1963-1973, 1988.
McNeall et al., *Gene*, 76:81, 1989.
Miksicek et al., *Cell*, 46:203, 1986.
Miller et al., *Am. J. Clin. Oncol.*, 15(3):216-221, 1992.
Mordacq and Linzer, *Genes and Dev.*, 3:760, 1989.
Moreau et al., *Nucl. Acids Res.*, 9:6047, 1981.
Mueller and B. Wold, *Science* 246, 780-786, 1989.
Muesing et al., *Cell*, 48:691, 1987.
Muzyczka, *Curr Top Microbiol Immunol*, 158:97-129, 1992.
Nabel and Baltimore, *Nature* 326:711-713, 1987.
Nakamura et al., In: *Handbook of Experimental Immunology* (4th Ed.), Weir et al., (eds). 1:27, Blackwell Scientific Publ., Oxford, 1987.
Naldini et al., *Science*, 272(5259):263-267, 1996.
Ng et al., *Nuc. Acids Res.*, 17:601, 1989.
Nicolas and Rubinstein, In: *Vectors: A survey of molecular cloning vectors and their uses*, Rodriguez and Denhardt, eds., Stoneham: Butterworth, pp. 494-513, 1988.
Nicolau and Sene, *Biochim. Biophys. Acta*, 721:185-190, 1982.
Nicolau et al., *Methods Enzymol.*, 149:157-176, 1987.
Nomoto et al., *Gene*, 236(2):259-271, 1999.
Ohara et al., *Proc. Nat'l Acad. Sci. USA*, 86: 5673-5677, 1989.
Omirulleh et al., *Plant Mol. Biol.*, 21:415-28, 1993.
Ondek et al., *EMBO J.*, 6:1017, 1987.
Omitz et al., *Mol. Cell. Biol.*, 7:3466, 1987.
Palmiter et al., *Nature*, 300:611, 1982.
Paskind et al., *Virology*, 67:242-248, 1975.
PCT Application PCT/US87/00880
PCT Application PCT/US89/01025
PCT Application WO 88/10315
PCT Application WO 90/07641
PCT Application WO89/06700
Pech et al., *Mol. Cell. Biol.*, 9:396, 1989.
Pelletier and Sonenberg, Nature, 334:320-325, 1988.
Perales et al., *Proc. Nat'l Acad. Sci. USA*, 91:4086-4090, 1994.
Perez-Stable and Constantini, *Mol. Cell. Biol.*, 10:1116, 1990.
Perou et al., *Nature* 406 (6797), 747-752, 2000.
Picard and Schaffner, *Nature*, 307:83, 1984.
Pinkert et al., *Genes and Dev.*, 1:268, 1987.
Ponta et al., *Proc. Nat'l Acad. Sci. USA*, 82:1020, 1985.
Porton et al., *Mol. Cell. Biol.*, 10:1076, 1990.
Potrykus et al., *Mol. Gen. Genet.*, 199:183-188, 1985.
Potter et al., *Proc. Nat'l Acad. Sci. USA*, 81:7161-7165, 1984.
Queen and Baltimore, *Cell*, 35:741, 1983.
Quinn et al., *Mol. Cell. Biol.*, 9:4713, 1989.
Redondo et al., *Science*, 247:1225, 1990.
Reisman and Rotter, *Mol. Cell. Biol.*, 9:3571, 1989.
Resendez Jr. et al., *Mol. Cell. Biol.*, 8:4579, 1988.
Ridgeway, In: *Vectors: A survey of molecular cloning vectors and their uses*, Stoneham: Butterworth, pp. 467-492, 1988.
Ripe et al., *Mol. Cell. Biol.*, 9:2224, 1989.
Rippe et al., *Mol. Cell Biol.*, 10:689-695, 1990.
Rittling et al., *Nuc. Acids Res.*, 17:1619, 1989.
Rosen et al., *Cell*, 41:813, 1988.
Roux et al., *Proc. Nat'l Acad. Sci. USA*, 86:9079-9083, 1989.
Sakai et al., *Genes and Dev.*, 2:1144, 1988.
Sambrook et al., In: *Molecular Cloning: A Laboratory Manual*, 2nd Ed., Cold Spring Harbor Press, Cold Spring Harbor, N.Y., 1989.
Satake et al., *J. Virology*, 62:970, 1988.
Schaffner et al., *J. Mol. Biol.*, 201:81, 1988.
Searle et al., *Mol. Cell. Biol.*, 5:1480, 1985.
Sharp and Marciniak, *Cell*, 59:229, 1989.
Shaul and Ben-Levy, *EMBO J.*, 6:1913, 1987.
Sherman et al., *Mol. Cell. Biol.*, 9:50, 1989.
Sleigh and Lockett, *J. EMBO*, 4:3831, 1985.
Spalholz et al., *Cell*, 42:183, 1985.
Spandau and Lee, *J. Virology*, 62:427, 1988.
Spandidos and Wilkie, *EMBO J.*, 2:1193, 1983.
Stephens and Hentschel, *Biochem. J.*, 248:1, 1987.
Sterling et al., How to Build a Beowulf: A Guide to the Implementation and Application of PC Clusters, The MIT Press, Cambridge, Mass. 1999.
Stuart et al., *Nature*, 317:828, 1985.
Sullivan and Peterlin, *Mol. Cell. Biol.*, 7:3315, 1987.
Swartzendruber and Lehman, *J. Cell. Physiology*, 85:179, 1975.
Takebe et al., *Mol. Cell. Biol.*, 8:466, 1988.
Tavernier et al., *Nature*, 301:634, 1983.
Taylor and Kingston, *Mol. Cell. Biol.*, 10: 165, 1990.
Taylor and Kingston, *Mol. Cell. Biol.*, 10:176, 1990.
Taylor et al., *J. Biol. Chem.*, 264:15160, 1989.
Temin, In: *Gene Transfer*, Kucherlapati (ed.), New York: Plenum Press, pp. 149-188, 1986.
Thiesen et al., *J. Virology*, 62:614, 1988.
Tratschin et al., *Mol. Cell. Biol.*, 4:2072-2081, 1984.
Treisman, *Cell*, 42:889, 1985.
Tronche et al., *Mol. Biol. Med.*, 7:173, 1990.
Trudel and Constantini, *Genes and Dev.* 6:954, 1987.

Tsumaki et al., *J Biol Chem.* 273(36):22861-22864, 1998.
Tur-Kaspa et al., *Mol. Cell Biol.,* 6:716-718, 1986.
Tyndell et al., *Nuc. Acids. Res.,* 9:6231, 1981.
Vannice and Levinson, *J. Virology,* 62:1305, 1988.
Vasseur et al., *Proc Natl. Acad. Sci. U.S.A.,* 77:1068, 1980.
Wagner et al., *Science,* 260:1510-1513, 1993.
Walker et al, *Proc. Nat'l Acad. Sci. USA,* 89:392-396 1992.
Wang and Calame, *Cell,* 47:241, 1986.
Wang et al., *Brain Pathol.,* 12:95-107, 2002.
Weber et al., *Cell,* 36:983, 1984.
Weinberger et al. *Mol. Cell. Biol.,* 8:988, 1984.
Wilson et al., *Science,* 244:1344-1346, 1989.
Winoto and Baltimore, *Cell* 59:649, 1989.
Wong et al., *Gene,* 10:87-94, 1980.
Wu and Wu, *J. Biol. Chem.,* 262:4429-4432, 1987.
Wu and Wu, *Adv. Drug Delivery Rev.,* 12:159-167, 1993.
Wu and Wu, *Biochemistry,* 27:887-892, 1988.
Wu et al., *Biochem Biophys Res Commun.,* 233(1):221-226, 1997.
Yang et al., *Proc Nat'l Acad. Sci. USA,* 87:9568-9572, 1990.
Yutzey et al. *Mol. Cell. Biol.,* 9:1397, 1989.
Zhao-Emonet et al., *Biochem. Biophys. Acta.,* 1442(2-3): 109-19, 1998.
Zufferey et al., *Nat Biotechnol,* 15(9):871-875, 1997.

What is claimed is:

1. A method of classifying a glioma comprising:
    (a) obtaining a primary glioma tumor sample;
    (b) measuring in cells of the tumor sample the mRNA or protein expression level of MAPKK1, HTF4, transducin β2, BMP2A, TrkB, DAP3, RAB3A, transcription elongation factor SII, integrin beta I, IGFBP2, NKEFB, HSP27, neuromodulin, and LIMK1;
    (c) comparing the mRNA or protein expression levels obtained in step (b) with the expression levels of the mRNAs or proteins in step (b) from at least a first known glioma cell type; and
    (d) classifying said tumor sample as glioblastome multiforme (GM) when the sample shows altered expression of IGFBP2, NKEPFB and one or more of HSP27, neuromodulin or LIMK1, anaplastic astrocytoma (AA) when the sample shows altered expression of MAPKK1 and one or both of BMP2A or HTF4, anaplastic oligodendroglioma (AO) when the sample shows altered expression of DAP3 and either TrkB and RAB3A, or transcription elongation factor II and integrin β1, or oligodendroglioma (OL) when the sample shows altered expression of transducin β2 based on the expression comparison in step (c).

2. The method of claim 1, wherein the tumor tissue sample is a needle biopsy, resected tumor or tumor fragment.

3. The method of claim 1, wherein the expression levels obtained in step (b) are compared with expression levels of the mRNAs or proteins in step (b) from least a second known glioma cell type.

4. The method of claim 1, wherein the expression levels obtained in step (b) are compared with expression levels of the mRNA or proteins in step (b) from least a third known glioma cell type.

5. The method of claim 1, wherein the expression levels obtained in step (b) are compared with expression levels of four known glioma cell types.

6. The method of claim 1, wherein the expression levels obtained in step (b) are compared with a database of expression levels obtained from a plurality of distinct samples each representing said first known glioma cell type.

7. The method of claim 5, wherein the expression levels obtained in step (b) are compared with a database of expression levels obtained from a plurality of distinct samples representing each of said four known glioma cell types.

8. The method of claim 1, further comprising making a decision regarding the treatment of the subject from which said tumor sample was obtained.

9. The method of claim 1, further comprising making a prediction on the efficacy of treating the subject from which said tumor sample was obtained.

10. The method of claim 1, further comprising making a prediction on the survival of the subject from which said tumor sample was obtained.

11. The method of claim 1, wherein the expression levels are determined by microarray analysis of transcripts.

12. The method of claim 1, wherein the expression levels are determined by multiplex PCR of transcripts.

13. The method of claim 1, wherein the expression levels are determined by immunohistochemistry.

14. The method of claim 11, wherein microarray analysis comprises use of oligonucleotides that hybridize to transcripts or cDNAs for the selected genes, and wherein the oligonucleotides are disposed on the surface of a chip or wafer.

15. The method of claim 14, wherein said oligonucleotides are about 25 to about 50 base pairs in length.

16. The method of claim 1, further comprising obtaining an expression level from cells of the tumor sample of transducin β1.

17. The method of claim 16, further comprising obtaining expression levels from cells of said tumor sample for one or more of GRB2, TIE-2, TNFSF5, and CREB1.

18. The method of claim 17, further comprising obtaining expression levels from cells of said tumor sample for one or more of MUC18, RXR-β, clusterin, erythropoietin receptor, BCL-W, CDK7, myc, CC chemokine receptor, JAK3, DNase X, GNA13, RAB5A, PKA C-α, DNA ligase IV, acidic fibroblast growth factor and preprotachykinin β.

19. The method of claim 17, further comprising obtaining expression levels from cells of said tumor sample for one or more of RAB3A, IL2R-γ, cyclin E, MAP kinase 10, BCL2A1, VEGFR2, CD11B, thymosin β10, and uPAR.

* * * * *